United States Patent
de la Huerga

(12) 
(10) Patent No.: US 6,259,654 B1
(45) Date of Patent: *Jul. 10, 2001

(54) MULTI-VIAL MEDICATION ORGANIZER AND DISPENSER

(75) Inventor: Carlos de la Huerga, River Hills, WI (US)

(73) Assignee: Telaric, L.L.C., Mequon, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/185,137

(22) Filed: Nov. 3, 1998

Related U.S. Application Data

(63) Continuation-in-part of application No. 09/168,783, filed on Oct. 8, 1998, which is a continuation-in-part of application No. 08/832,613, filed on Mar. 28, 1997, now Pat. No. 5,852,590, and a continuation-in-part of application No. 08/955,475, filed on Oct. 21, 1997, now Pat. No. 6,032,155, which is a continuation-in-part of application No. 08/834,634, filed on Apr. 14, 1997, now Pat. No. 5,960,085.

(51) Int. Cl.[7] .................................................. G04B 37/00
(52) U.S. Cl. .............................................................. 368/10
(58) Field of Search .............................. 368/10, 107–113; 221/2, 3, 15; 340/309, 4; 364/569

(56) References Cited

U.S. PATENT DOCUMENTS

| | | |
|---|---|---|
| Re. 35,743 | 3/1998 | Pearson . |
| 3,227,127 | 1/1966 | Gayle . |
| 3,762,601 * | 10/1973 | McLaughlin ............................ 368/10 |
| 4,207,992 | 6/1980 | Brown . |
| 4,360,125 | 11/1982 | Martindale . |
| 4,437,579 | 3/1984 | Obland . |
| 4,483,626 | 11/1984 | Noble . |
| 4,504,153 * | 3/1985 | Schollmeyer et al. ................. 368/10 |
| 4,526,474 | 7/1985 | Simon . |
| 4,573,606 | 3/1986 | Lewis . |
| 4,616,316 | 10/1986 | Hanpeter . |
| 4,617,557 | 10/1986 | Gordon ................................. 340/568 |
| 4,626,105 | 12/1986 | Miller . |
| 4,664,289 | 5/1987 | Shimizu .................................... 221/2 |
| 4,674,651 | 6/1987 | Scidmore . |
| 4,674,652 | 6/1987 | Aten ......................................... 221/3 |
| 4,695,954 | 9/1987 | Rose . |
| 4,725,997 | 2/1988 | Urquhart . |
| 4,732,411 | 3/1988 | Siegel .................................... 283/75 |
| 4,733,362 | 3/1988 | Haraguchi ............................ 364/479 |

(List continued on next page.)

Primary Examiner—Bernard Roskoski
(74) Attorney, Agent, or Firm—Sokol Law Office

(57) ABSTRACT

This invention relates to a medication container that organizes several vials or cassettes of different types of medication by securing the vials to a unitary lid. A machine readable memory strip is affixed to each vial. Each memory strip contains prescription information and medication information pertaining to the medication in the vial. The unitary lid is equipped with sensors that read each memory strip and transmit the information to the computer processor and its associated memory device. The processor determines when each medication is to be taken and signals the patient to take the appropriate medication from the appropriate vial at the appropriate time. Indicator lights and a display are provided for this purpose. The vials are standard or slightly modified childproof pill containers, but can take the form of a blister pack dispenser or other containers as well. The lid is provided with a mechanism for dispensing or allowing the removal of medication from the vials, and obtaining actual medication consumption information based on when the pill is dispensed or when the lid is opened. This actual consumption information is used to keep inventory information regarding the number of each type of medication doses remaining in the container. The memory strips can be machine readable and writable so that they can be altered to include actual consumption information and inventory information. The automated lid contains a receiver for obtaining updated medication dosing information based on current laboratory tests or physical observations of the physician regarding the patient.

48 Claims, 19 Drawing Sheets

U.S. PATENT DOCUMENTS

| | | |
|---|---|---|
| 4,733,797 | 3/1988 | Haber ........................................ 221/8 |
| 4,785,969 | 11/1988 | McLaughlin . |
| 4,811,764 | 3/1989 | McLaughlin . |
| 4,823,982 | 4/1989 | Aten . |
| 4,839,806 | 6/1989 | Goldfischer ..................... 364/413.02 |
| 4,847,764 | 7/1989 | Halvorson ...................... 364/413.02 |
| 4,857,713 | 8/1989 | Brown . |
| 4,857,716 | 8/1989 | Gombrich ............................ 235/462 |
| 4,911,327 * | 3/1990 | Shepherd et al. ...................... 368/10 |
| 4,939,705 | 7/1990 | Hamilton . |
| 4,953,745 | 9/1990 | Rowlett . |
| 4,971,221 * | 11/1990 | Urquhart ................................. 368/10 |
| 4,984,709 | 1/1991 | Weinstein . |
| 5,014,875 | 5/1991 | McLaughlin ............................. 221/2 |
| 5,047,948 | 9/1991 | Turner . |
| 5,088,056 | 2/1992 | McIntosh . |
| 5,099,463 | 3/1992 | Lloyd . |
| 5,176,285 | 1/1993 | Shaw ........................................ 221/3 |
| 5,181,189 | 1/1993 | Hafner . |
| 5,208,762 | 5/1993 | Charbut ................................ 364/478 |
| 5,213,232 | 5/1993 | Kraft . |
| 5,233,571 | 8/1993 | Wirtschafter . |
| 5,273,318 | 12/1993 | Gorman . |
| 5,289,157 * | 2/1994 | Rudick et al. ......................... 368/10 |
| 5,313,439 | 5/1994 | Albeck . |
| 5,347,453 | 9/1994 | Maestre . |
| 5,392,952 | 2/1995 | Bowden . |
| 5,401,059 | 3/1995 | Ferrario ................................. 283/67 |
| 5,405,048 | 4/1995 | Rodgers ............................. 221/211 |
| 5,408,443 | 4/1995 | Weinberger . |
| 5,460,294 | 10/1995 | Williams ................................. 221/2 |
| 5,472,113 | 12/1995 | Shaw . |
| 5,480,062 | 1/1996 | Rogers ................................ 221/174 |
| 5,502,944 | 4/1996 | Kraft ...................................... 53/55 |
| 5,508,499 | 4/1996 | Ferrario ............................... 235/375 |
| 5,522,525 | 6/1996 | McLaughlin . |
| 5,609,268 | 3/1997 | Shaw ........................................ 221/2 |
| 5,623,242 | 4/1997 | Dawson ........................... 340/311.1 |
| 5,745,366 | 4/1998 | Higham .......................... 364/479.12 |
| 5,826,217 | 10/1998 | Lerner . |
| 5,852,590 * | 12/1998 | de la Huerga ........................ 368/10 |

* cited by examiner

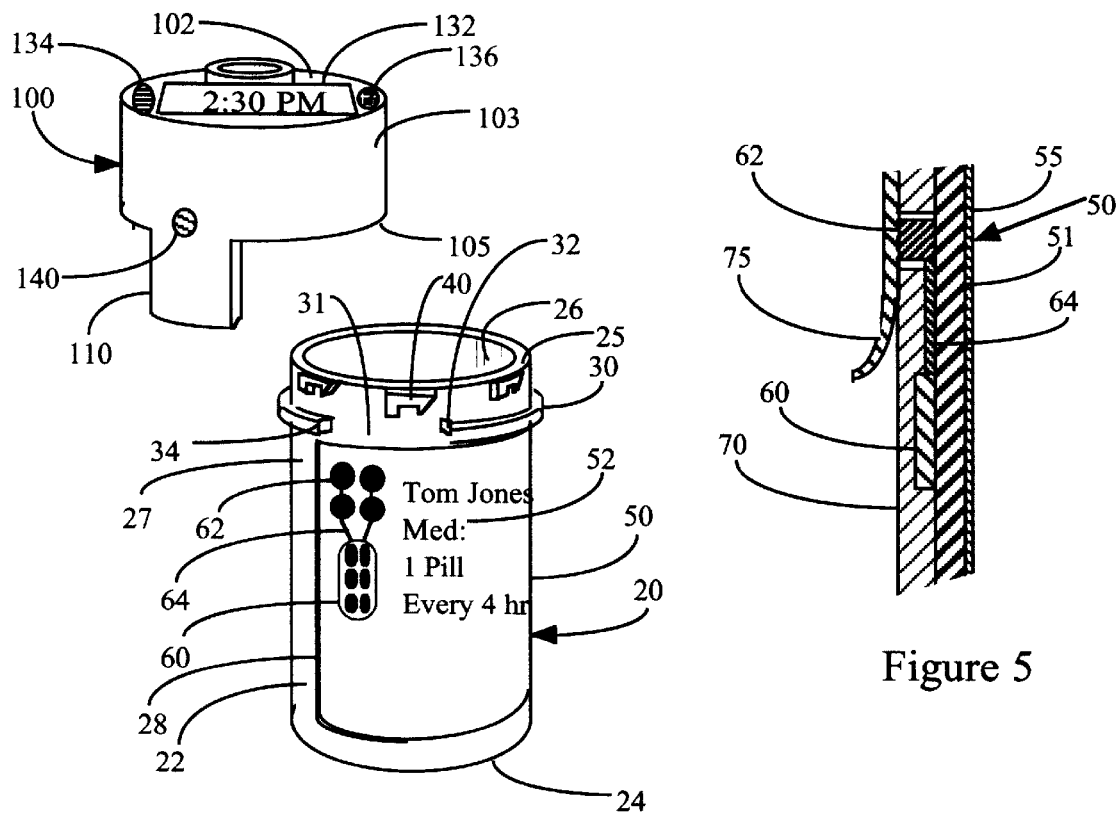
Figure 3
Figure 5
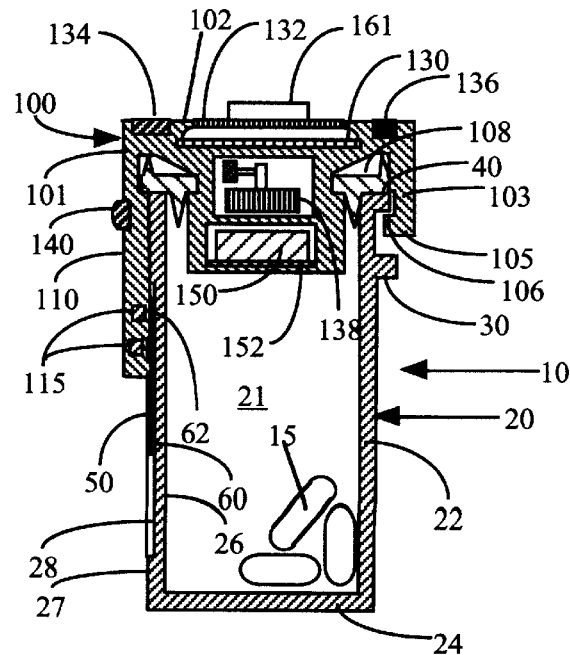
Figure 4

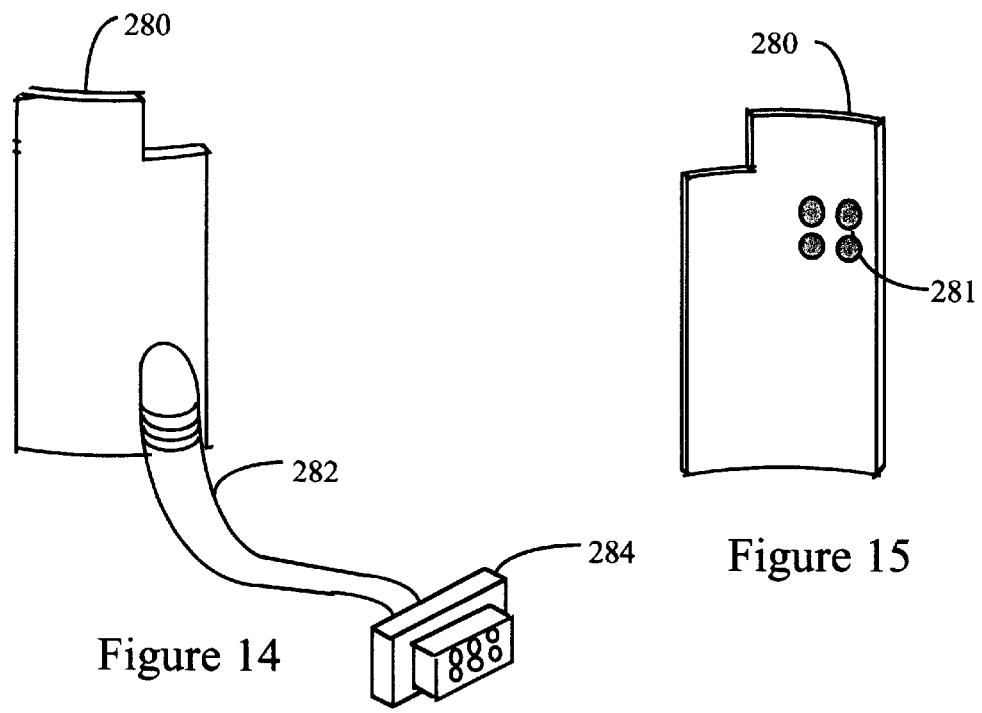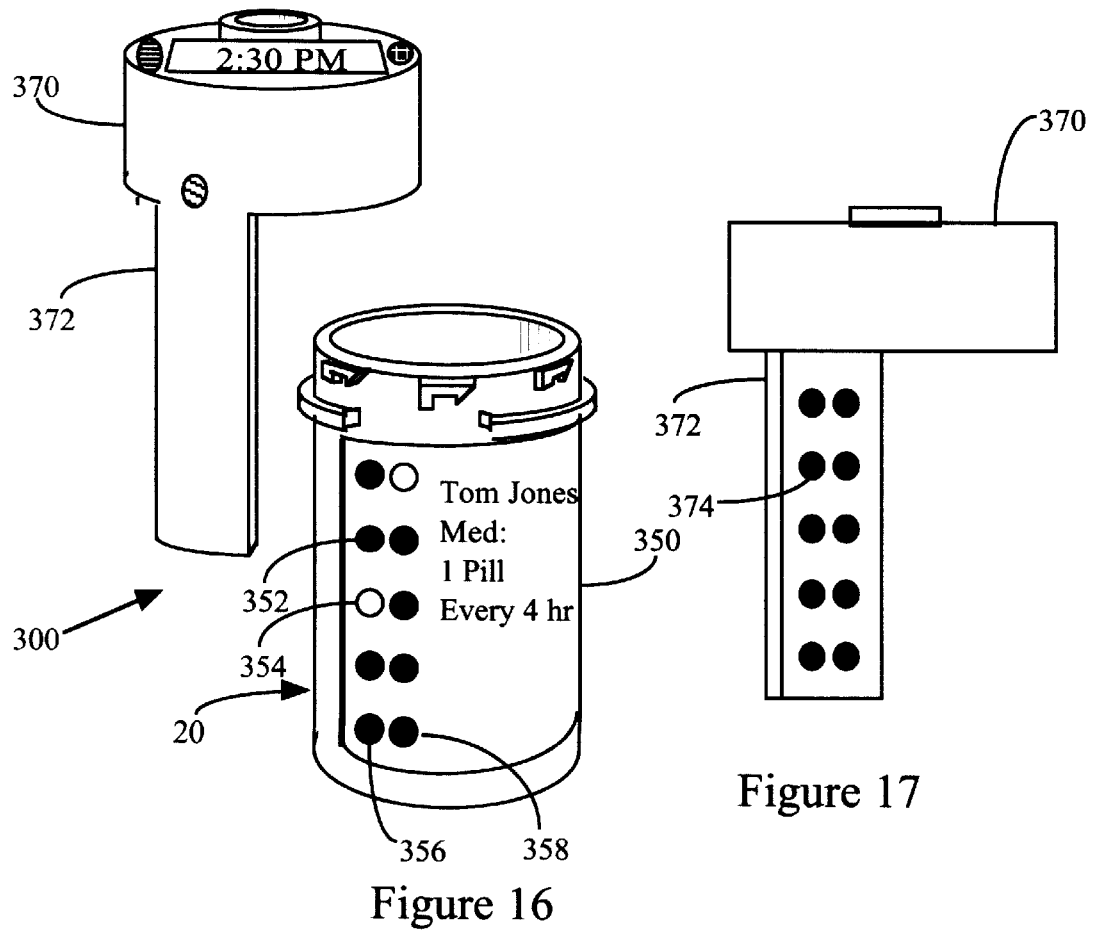

MULTI-VIAL MEDICATION ORGANIZER AND DISPENSER

This is a Continuation-In-Part of U.S. patent application Ser. No. 09/168,783 filed Oct. 8, 1998 which is a CIP of Ser. No. 08/832,613 filed Mar. 28, 1997 now U.S. Pat. No. 5,852,590 which is a Continuation-in-Part of Ser. No. 08/955,475 filed Oct. 21, 1997 now U.S. Pat. No. 6,032,155 which is a Continuation-in-Part of Ser. No. 08/834,634 filed Apr. 14, 1997 now U.S. Pat. No. 5,960,085.

TECHNICAL FIELD

This invention relates to a medication container that organizes several vials or cassettes of different types of medication by securing the vials to a unitary lid equipped with a computer processor that reads an information strip affixed to each vial and signals when medication is to be dispensed from each vial.

BACKGROUND

Medication containers that remind a patient to take their medication or keep track of the number of doses of medication in the container are well known. Examples of such automated containers are disclosed in U.S. Pat. Nos. 3,227,127 (Gayle); 4,207,992 (Brown); 4,360,125 (Martindale); 4,483,626 (Noble); 4,504,153 (Schollmeyer); 4,526,474 (Simon); 4,573,606 (Lewis); 4,695,954 (Rose); 4,725,997 (Urguhart); 4,939,705 (Hamilton); 4,984,709 (Weinstein); 5,099,463 (Lloyd); 5,181,189 (Hafner); 5,213,332 (Kraft); 5,313,439 (Albeck); 5,392,952 (Bowden); 5,472,113 (Shaw) and 522,525 (McLaughlin), the disclosures of which are incorporated by reference.

The general purpose of an automated container is to improve patient compliance in taking the appropriate medication on schedule. While taking a particular medication on a regular schedule may seem a simple process, it is often difficult to accomplish, especially when the patient has been prescribed to take several medications. Dosing regimens that require the patient to take different doses of different medications at different times can be particularly confusing. For example, a prescription that requires a patient to take two doses of medication A and one dose of medication B can be confusing. A patient can inadvertently take one dose of medication A and two doses of medication B. In addition, some medications are taken in a paired dosing regimen, with medication A being taken on Monday, medication B being taken on Tuesday, medication A on Wednesday, etc. Other medications are not intended to be taken together at all because they either neutralize each other or cause adverse side effects that can result in illness or even death. This situation is particularly problematic when more than one physician is prescribing medication to the patient. Conventional medication containers designed for a patient's personal use on an out-patient basis do not assist the patient in taking the correct medication at the correct time, particularly when several medications have been prescribed.

The ability to comply with prescribed medication dosing requirements is complicated in situations where dosing amounts change over time. For example, prescribed dosing amounts are frequently a function of ongoing laboratory tests that determine the patient's medication needs. In these situations, physicians need to be able to easily communicate changes in dosing amounts to their patients as quickly as possible. Medication compliance is particularly important when powerful medications are prescribed, and over-medicating or under-medicating a patient can lead to serious side effects, illness and even death. Yet, keeping patients in hospitals for a prolonged period of time to ensure that dosing regimens are changed when necessary is not considered a practical solution.

The process of taking several medications at the appropriate time is further complicated if the medication or an illness causes the person to think less clearly or to be forgetful. There is the anxiety of being uncertain if you took the medication earlier in the day. Then, there is the problem of patients completely forgetting to take their medication. The first condition is alleviated by simply indicating when the medication is to be taken next. If the container indicates a future time or day to take the next medication, the patient knows that they have taken the current dosage. If the container indicates a present or past time, the patient knows that they should take the medication now. To solve the problem of completely forgetting to take a dosage of medication, a container will typically contain an alarm to remind the patient to take the medication. Unfortunately, the presently available products and the above patents suffer from one or more problems or limitations.

One problem in reminding patients to take their medication on time is that many automated medication systems are not transportable and not intended for use on an out-patient basis. This is especially true of systems that handle complicated dosing regimes, handle a variety of medications, or provide fairly detailed information about the medications being consumed. Yet, many patients are not home bound. In fact, the purpose of many medications is to enable people that would otherwise be incapacitated to live normal, ambulatory lives. To be effective, medication alerting methods must be easily transportable, not just an in-home alarming system.

An additional problem is childproofing the automated medication container. Childproofing is frequently necessary to prevent an infant, child, or mentally handicapped or medicated person from gaining unsupervised access to the medication. The childproofing features must cooperate with the automated features of the container.

A further problem is that some automated dispensers dispense a variety of different pills at the same time. Some dispensers empty a preloaded number of pills from the container as it passes over an open dispensing chute. If the patient does not take all the medication, there is no place to put the excess. The medication either remains in the dispensing area, possibly resulting in an accidental overdose at a later time or consumption by a child, or the medication is thrown out. If an attempt is made to reload the medication into the dispenser, the dispensing patterns can be inadvertently altered. This is particularly problematic if the dispenser is handling medications that are similar in appearance.

A still further problem is that errors can occur when a care giver removes a variety of medications from the pharmacist supplied containers and inserts the medications into a different medication container or machine. An example being a container with separate compartments marked "breakfast, lunch and dinner", or "Monday, Tuesday, Wednesday, etc." In fact, there is some question regarding the legality of a care giver removing medications from pharmacist supplied containers and placing them into other containers. There is good reason for caution regarding the shuffling of medication from one container to another. Given the strength of many medications in use today, any confusion about the medications put in the secondary container or any confusion regarding the prescription regimens could have a significant adverse affect on the patient.

A still further problem is that the patient must program a timing or alarming mechanism in an automated dispenser by manual entry of additional coded data. A magnetic strip or smart card can also be used to enter the data. Unfortunately, the cards are easily misplaced and errors can result if the wrong data is entered into the dispensing machine manually or via an incorrect card. In addition, such dispensing machines have to be returned to the pharmacist frequently for reprogramming when a new medication is prescribed.

A still further problem is that many medication containers do not provide a means for counting the number of pills remaining in the container or the number of pills taken to date. The patient or care giver must manually enter the amount of medication dispensed or account for the quantity of medication remaining after each dose is consumed. In situations where the unused portion of a prescribed medication is returned to the pharmacy, such as in a hospital setting, the pharmacist must manually count the number of pills left in the container.

A still further problem with conventional automated medication containers is that they do not record the actual dosing regimen taken by the patient. A patient could take the medication too early, too late or completely miss taking the medication at various times. This results in a sporadic actual consumption or dosing regimen for the medication. The containers in use today do not provide an easy method of communicating the sporadic extent of the actual consumption regimen to the patient, or their pharmacist or physician.

A still further problem in designing an automated medication container is that the container should be compatible with conventional, non-automated medication containers used by the pharmaceutical industry today. See FIG. 1. A dramatic deviation from the conventional design would inhibit the adoption of the automated container design. A compatible design would enable the pharmacist to continue using conventional, non-automated containers in situations where such a container is appropriate, but would enable the pharmacist to provide an automated container in situations where this type of container is appropriate.

A still further problem with designing an automated medication container is that the more expensive automated components should be reusable. The increased cost of providing a microprocessor, memory displays, alarms and circuitry in a container would likely be prohibitive if the entire container disposed of after a single prescription is consumed. As many components as possible must be designed to be reused.

The present invention overcomes these and other limitations in existing medication dispensing products.

SUMMARY OF THE INVENTION

This invention relates to a medication container that organizes several vials or cassettes of different types of medication by securing the vials to a unitary lid. A machine readable memory strip is affixed to each vial. Each memory strip contains prescription information and medication information pertaining to the medication in the vial. The unitary lid is equipped with sensors that read each memory strip and transmit the information to the computer processor and its associated memory device. The processor determines when each medication is to be taken and signals the patient to take the appropriate medication from the appropriate vial at the appropriate time. Indicator lights and a display are provided for this purpose. The vials are standard or slightly modified childproof pill containers, but can take the form of a blister pack dispenser or other containers as well. The lid is provided with a mechanism for dispensing or allowing the removal of medication from the vials, and obtaining actual medication consumption information based on when the pill is dispensed or when the lid is opened. This actual consumption information is used to keep inventory information regarding the number of each type of medication doses remaining in the container. The memory strips can be machine readable and writable so that they can be altered to include actual consumption information and inventory information. The automated lid contains a receiver for obtaining updated medication dosing information based on current laboratory tests or physical observations of the physician regarding the patient.

One advantage of the present medication container invention is to improve patient compliance in selecting the appropriate medication from several vials of different medications, and taking that appropriate medication on schedule. The invention is of particular use when the patient has been prescribed to take several medications with dosing regimens that require the patient to take different amounts or doses of different medications at different times. The automated lid can easily instruct the patient to take two doses of medication A by lighting an indicator light by the appropriate vial and displaying a message to take two pills. Once medication A has been dispensed, the lid can instruct the patient to take on dose of medication B in a similar manner. This prevents a patient from inadvertently taking one dose of medication A and two doses of medication B. The automated lid is also helpful when medications are taken in a paired dosing regimen, with medication A being taken on Monday, medication B being taken on Tuesday, medication A on Wednesday, etc. The lid indicates when each medication is to be taken so that the patient does not have to rely on his or her memory. The container is even programmed to display a message stating when the last dose of medication A or B was dispensed or when the next dose of medication A or B is due.

Another advantage of the present invention is that contraindication information is stored on each information strip and transmitted to the automated lid. The automated lid will sound or otherwise indicate a warning when vials of two different medications are secured to the lid that are not intended to be taken together. This is particularly advantageous in the relatively common situation where several physicians are prescribing different medication to the same patient, and the patient is being handled on an out-patient basis.

A further advantage of the present invention is that the patient can quickly receive updated dosing information on an out-patient basis via a portable paging device, and transmit that information to the automated lid. The patient does not need to go to the physicians to obtain a new written prescription or to a pharmacy to obtain a new vial with new dosing instructions. This is desirable when prescribed medication dosing requirements change over time, such as in situations where ongoing laboratory tests are used to determine the patient's medication needs. The quickness of this system of sending updated medication dosing information to a patient is particularly important when powerful medications are prescribed, and over-medicating or under-medicating a patient can lead to serious side effects, illness and even death. The quickness of the system enables a patient to live a more normal life while receiving treatment on an out-patient basis, avoids a prolonged hospital stay and helps to reduce the cost of treating the individual.

A still further advantage of the present invention is that the interactive label contains a wide variety of information that is not practical to print out in textual form on a relatively small label. The memory or memory strip contains information regarding the number of pills or capsules to be taken per dosage and the dosing regimen, e.g. daily, four times a day, before a meal, etc. The memory strip also contains information regarding the medication, such as the medication name, expiration date, quantity in container, patient name, pharmacy name, address and telephone number, pharmacy prescription number, prescribing doctor name and telephone number.

A further advantage of the present invention is that the memory strip contains special prescription requirements and instructions that are expressed in the form of a series of processor instructions such as those written in the Java or other computer language, as opposed to a simple four times per day dosing regime. The prescription requirements can, for example, indicate frequent dosages of a medication when starting a medication, then indicate a gradual reduction of medication, and finally indicate a sustained steady dose after several days.

A further advantage or the present invention is that the memory strip can contain prescription requirements that include instructions for alternating between differing medications in a controlled sequence. For example, some advances in Acquired Immune Deficiency Syndrome (AIDS) medication protocols require the patient to consume two or more medications, but on alternating or sequential days. Although each medication is held in a separate container, the memory strip on each medication container could provide instructions on taking both medications.

A still further advantage of the present invention is that the interactive label is compatible with the vials used in standard or slightly modified pharmacist supplied medication containers. Special vials are not necessary. Medication can be inserted in standard or slightly modified pharmacist supplied container and a memory strip affixed to the vial. Patients can then replace the standard cap for the container with an automated cap to obtain the information in the memory strip.

A still further advantage of the present invention is that the interactive label can provide sufficient information to enable a single container to hold and dispense a variety of medications. Although the medications would have to be sufficiently different looking in appearance to avoid confusion, the memory strip can provide enough detailed information to provide the patient with instructions for taking all the types of medication in the container. Such a medication container would alleviate the need for the patient to carry around several containers at once.

A still further advantage of the present invention is that the memory strip can be secured to a container via the use of a textual label or the strip can be secured directly to the medication container itself The memory strip need not be secured to a label. This flexibility facilitates the use of the memory strip on a variety of containers depending on the intended function and manufacturing costs of the container.

A still further advantage of the present invention is that actual medication consumption information can be downloaded into the memory strip. This enables the patient to keep the more expensive automated cap, and return the vial and memory strip to the pharmacist or physician for analyzing the patient's response to and the effectiveness of the medication. The pharmacist or physician can read the information on the memory strip via a separate sensing element kept in their office.

A still further advantage of the present invention is that the microprocessor, memory sensors, display and alarms are located in the cap of the container. The memory strip is affixed to the container vial. This enables a patient to reuse the automated cap for different prescriptions. The vial and the memory strip which contains information specific to the prescription for the medication in the container can be discarded or returned to the pharmacist or physician. The more expensive automated cap is reused for subsequent prescriptions, thereby reducing the long term cost of the automated container.

A still further advantage of the present invention is that the information in the interactive label and the microprocessor memory is used to alert the patient when it is time to take a dose of medication and how many pills or capsules to consume. The interactive label and microprocessor are also used to warn the patient to defer taking medication at the present time, or indicate at what time the next dose of medication is to be taken. These alarms and indicators should increase patient compliance in taking medication according to the prescribed regimen.

A still further advantage of the present invention is that the automated medication container can convey information to a separate device such as a patient's home computer to aid in alerting the patient to take the medication in a timely manner. For example, the patients' home computer can page the patient when it is time to take a dose of medication.

A still further advantage of the present invention is that the interactive label and automated cap are compatible with a conventional medication container having a cylindrical vial and childproof cap. See FIG. 1. The pharmacist can dispense medication in a standard or slightly modified childproof container affixed with the interactive label. The patient is then free to replace the conventional childproof cap with an automated childproof cap.

The conventional medication vial can be easily modified to facilitate use with the interactive label. The slightly modified vial includes a guide and limiting ring molded around the periphery of the vial. The interactive label is aligned with an opening in the ring. A sensing tab in the cap extends through the opening in the ring and over the contacts for the memory strip. The ring ensures the unique placement of a sensing tab when the appropriate automated cap is secured to the vial. When properly closed, the sensing tab electronically reads the electronic memory strip. The ring does not interfere with the operation of the standard commercially available cap or the automated childproof cap.

A still further advantage of the invention is that the automated cap includes a battery or photo cell, a microprocessor with a timing circuit, and a LCD display. The timing circuit enables the cap to provide the time of day, day of the week or date to the patient A still further advantage of the present invention is that the medication container checks to ensure that the patient secured the automated cap to its corresponding vial. When the automated cap is attached to a vial having an interactive label, a check is made to determine if the cap was previously attached to this vial by comparing the prescription information now being sensed and read to the information previously stored in the memory of the microprocessor in the cap. If the information is the same as previously recorded, a notation is made that the patient probably just consumed a dosage of the medication and the timing program is adjusted to alert the patient to take the next dose after the appropriate time passes. If the information is different from that previously recorded, the patient is alerted to the possibility that the cap has been placed on the wrong medication container. The patient can then remove the cap and place it on the correct container. Alternately, the patient can ignore the alert and allow it be to automatically canceled after a time period passes or can manually cancel the alert by pressing a button on the cap. In each case, the new information is copied into the internal memory of the automated cap and an indication is made to the patient that they can take the medication according to the present memory strip prescription instructions.

An additional advantage of the present invention is that it can be used to record actual medication consumption information. The timing circuit enables the automated cap to obtain actual consumption information by recording when the cap is removed from the medication vial. Removal of the cap disrupts the alignment of the sensing tab with the contacts of the memory strip. This disruption or returning the cap to seal the vial establishes the time and date the user consumed the medication. The prescription timing regimen is used to compute the next time the patient should take the medication. When the cap is replaced and the information in the memory strip matches the information previously recorded into the memory of the microprocessor, the microprocessor determines that the user just removed the cap, consumed a dose of medication, and replaced the cap.

A still further advantage of the present invention is that the cap computes the next time the patient is to take the medication and displays this information to the patient. The time and or date or day is displayed via a display such as a LCD device in the cap. By reading the display, the user can easily and reliably determine the next time to take the medication. The LCD display includes the number of pills or capsules to be consumed. Given enough display area, specific instructions for taking the medication will be presented, e.g., "consume 2 hours before eating."

A still further advantage of the present invention is that the cap can alert the patient to take the medication by sounding an audible alarm, illuminating an indicator such as an LCD, or rotating an eccentrically positioned weight to cause a vibration alert. These alarms should improve patient compliance.

A still further advantage of the present invention is that prescription information on the memory strip is conveyed to the patient's personal home computer, or a hospital or nursing home computer. The information on the memory strip controls additional alerting means, such as additional light sources, audible alarms, via telecommunication to call the patient at home or office depending on the time of day to remind the patient to take the medication. The patient can respond by using the telephone keypad to indicate whether a dose was taken. In this way, patient compliance with the physician prescription can be tracked. Alternately, the personal home computer can page the patient to indicate which medication is to be taken. The memory strip information is copied to the home or business personal computer via a separate sensing element capable of communicating with the personal or business computer. The container can also be equipped with an infrared transmitter activated by the patient to send the memory strip information to the personal computer.

A still further advantage of the present invention is that the childproof container helps prevent the patient from taking medication too soon or too frequently. The cap is equipped with a locking mechanism that interacts with the childproof locking features. When the cap is in place, a solenoid activated armature prevents any attempt to open the cap until the appropriate time for taking the medication. When it is time to consume the medication, the solenoid releases the armature. The locking mechanism can also limit the number of times a day the patient can gain access to medication that is consumed on an as needed basis, e.g. medication used to control pain. This helps prevent the patient from taking the medication too many times in any given day or from repeating dosages of the medication within too short a time period.

A still further advantage of the present invention is that the interactive label is compatible with a multi-dose blister pack. The blister pack can be prepackaged by the original manufacturer or by a local pharmacy. The interactive label is then affixed to a surface of the blister pack. The label includes the memory strip and textual information regarding the medication prescription.

A still further advantage of the present invention is that the blister pack and interactive label can be inserted into a dispenser having a compatible sensing element, microprocessor, memory sensors, optional alerting device LCD display. This dispenser alerts the patient when to take medication, helps ensure that the medication is not accessible to a child (childproof), prevents the patient from taking too much medication or taking it prematurely, and indicates when the medication supply is being exhausted to allow the patient adequate time to obtain a refill of the prescription. The dispenser also includes a mechanism for assisting the patient in dispensing the medication on from the blister pack.

Other advantages and aspects of the invention will become apparent upon review of the specification, claims and drawings.

BRIEF DESCRIPTION OF THE DRAWINGS

FIG. 3 is a perspective view of the first embodiment of the invention showing the automated cap removed from the vial to reveal the electrical contacts of the memory strip FIG. 4 is a cross sectional, side plan view of the first embodiment of the invention showing the electronic memory strip and its electrical contacts on the wall of the vial, and an automated cap with a resilient sealing disc, battery, audio, illuminating and vibrational alarms.

FIG. 5 is an enlarged, cross-sectional, side plan view of the interactive label showing the memory strip, electrical contacts, adhesive coating, protective coating and removable insulating layer.

FIG. 14 is a front perspective view showing a sensing device used to convey information in the memory strip of the medication container to a separate computer.

FIG. 15 is a rear perspective view of the sensing device showing the sensors that engage the electrical contacts of the memory strip.

FIG. 16 is a perspective view of a third embodiment of the present invention where the medication container includes a cylindrical vial with an interactive label having a plurality of conductive or reflective surfaces, and an automated cap that seals the open end of the vial.

FIG. 17 is an elevation view of the automated cap for the third embodiment of the invention showing a plurality of sensors on the inside of the cap that sense the conductive or reflective surfaces of the interactive label.

DETAILED DESCRIPTION

Figure 1:
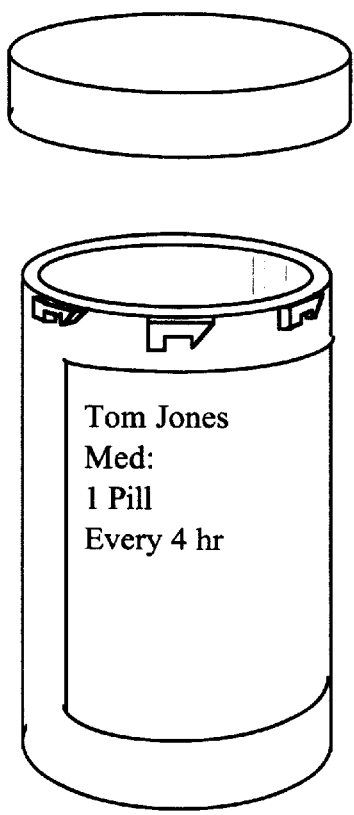
FIG. 1 is a perspective view of a conventional, childproof, medication container consisting of a cylindrical vial and a removable cap.

The present invention relates to a medication container with an interactive label. While the invention is susceptible of embodiments in many different forms, there are shown in the drawings and will herein be described, several forms of the invention with the understanding that the present disclosure is to be considered as an exemplification of the principles of the invention, and is not intended to limit the broad aspects of the invention to the several embodiments illustrated.

First Embodiment

Figure 2:
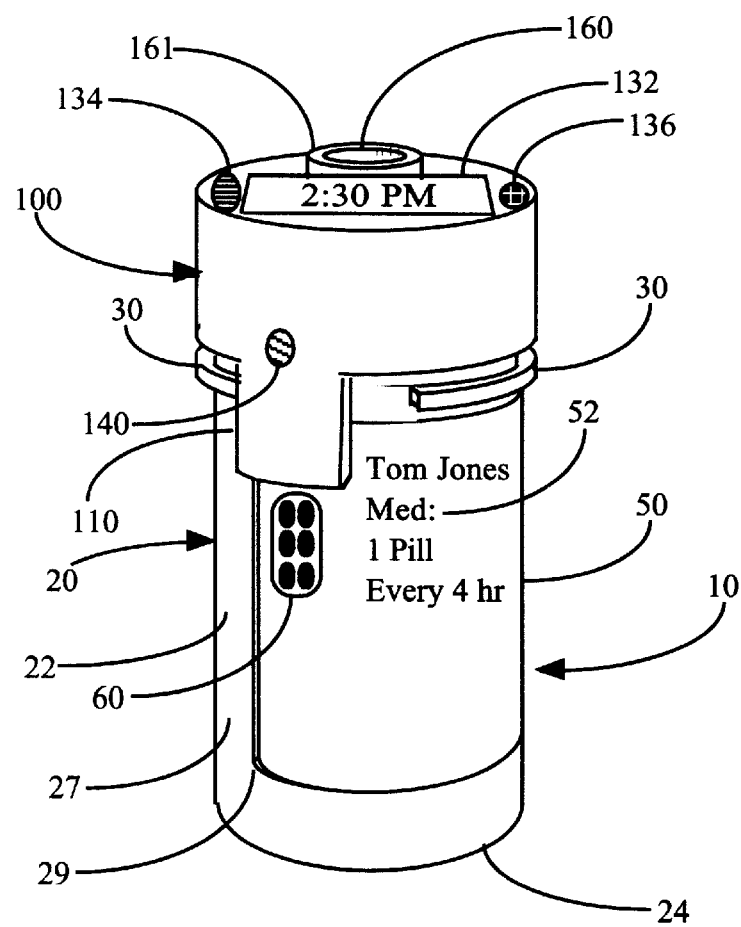
FIG. 2 is a perspective view of a first embodiment of the present invention where the medication container includes a cylindrical vial with an interactive label having an electronic memory strip, and an automated cap that seals the open end of the vial.

FIGS. 2–11 show a first embodiment of the invention where the container 10 includes a vial 20 with an interactive label 50 and an automated cap 100 with a sensing tab 110 for reading the electronically stored information 80 on the label and a computer processor 120 for controlling a visual display and a variety of alarms. As best shown in FIGS. 2–4, the vial 20 includes a compartment 21 defined by a cylindrical wall 22, a closed bottom end 24 and an open top end 25. Medication 15 is inserted into and removed from the compartment 21 via the open end 25 of the vial 20. The cylinder has an inner surface 26 and an outer surfaces 27. The vial 20 is made of a unitary piece of relatively rigid plastic similar to other conventional vial-type medication containers.

The vial 20 includes a first means for aligning the interactive label 50 with a predetermined location of the wall 22. This alignment means is accomplished by forming a recess 28 in the outer surface 27 of the wall 22. The recess 28 is defined by an inwardly projecting ridge 29 that extends around the perimeter of the recess. While this first alignment means is shown as recess 28, it should be understood that it could take on a variety of forms. For example, an outwardly projecting ridge (not shown) protruding from the wall 22 of the vial 20, or a raised substantially flat platform (not shown) protruding from the wall could be used. It should also be understood that the label 50 could be located on the inside surface 26 of the vial 20 without departing from the broad aspects of the invention.

The vial 20 includes a second or means for aligning the automated cap 100 with the vial 20 so that the sensing tab 110 of the cap is properly aligned with the interactive label 50 as discussed below. The second alignment means is accomplished by a guide ring 30 protruding from the outer surface 27 of the vial 20. The guide ring 30 is located at a substantially uniform, predetermined distance from the open end 25 of the vial. The guide ring surrounds most of the wall 22 of the vial. The guide ring has an opening 31 defined by its two ends 32 and 34. The ends 32 and 34 of the guide ring 30 are spaced apart a predetermined distance so that opening 31 has a predetermined size for accommodating sensing tab 110 as discussed below. While the second alignment means is shown and described as being guide ring 30, it should be understood that the second alignment means could take on other forms without departing from the broad aspects of the invention.

The vial 20 has several securement ratchets 40 for securing and sealing the cap 100 against the open end 25 of the vial. The ratchets 40 are evenly spaced around the open end 25, and protrude from the outer surface 27 of the vial 20. The ratchets are similar to those found on conventional child-proof medication containers as in FIG. 1. Each ratchet includes a cup portion 42, a top surface 44, a wedge 45 and a side surface 46. Although the ratchets 40 are shown and described as being evenly spaced from each other as in a conventional vial, it should be understood that one or more of the ratchets could be offset. Such an offset arrangement could be used to accomplish the second alignment means in lieu of guide ring 30.

As best shown in FIGS. 3–5, medication container 10 includes interactive label 50. The label 50 is affixed in the recess 28 in the wall 22 of the vial 20 so that the left edge of the label abuts and is aligned with the ridge 29 forming the left side of the recess. The upper edge of the label 50 abuts the ridge forming the upper side of the recess 28. This alignment positions the label 50 into its desired location on the wall 22 of the vial 20.

The interactive label 50 includes a paper backing 51 sized to fit in recess 28. The front surface of the paper backing 51 has a textual portion 52. The textual portion 52 includes textual information such as the patient's name, the medication name, the dosing regimen (e.g., daily, four times a day, etc.), the number of pills or capsules to consume during each dose, and any special instructions regarding the proper consumption of the medication (e.g., take an hour before meals). The rear surface of the backing paper 51 includes an adhesive coating 55 for affixing the label in the recess 28 of the wall 22 of the vial 20.

The interactive label 50 includes an electronic, machine readable and writable memory strip 60. The memory strip 60 is similar to those used in commercially available smart cards. The memory strip 50 includes contacts 62 that are in electrical communicate with the information 80 in the memory strip 60 via links or electrical connections such as wires 64 as discussed below. A protective coating 70 is applied over the memory strip 60. The protective coating 70 has holes aligned over each electrical contact 62. A removable insulating layer 75 is used to prevent premature communication with the memory strip 60 before the patient begins taking the medication 15. Although the memory strip 60 is shown and described as being secured to a paper backing 51, it should be understood that the memory strip 60 could be affixed directly to the inner or outer surface 26 or 27 of the vial 20 or even imbedded in the vial. While the memory device 60 is described and shown as having the shape of a strip, it should be understood that differently shaped memory devices could be used without departing from the invention.

Figure 8:
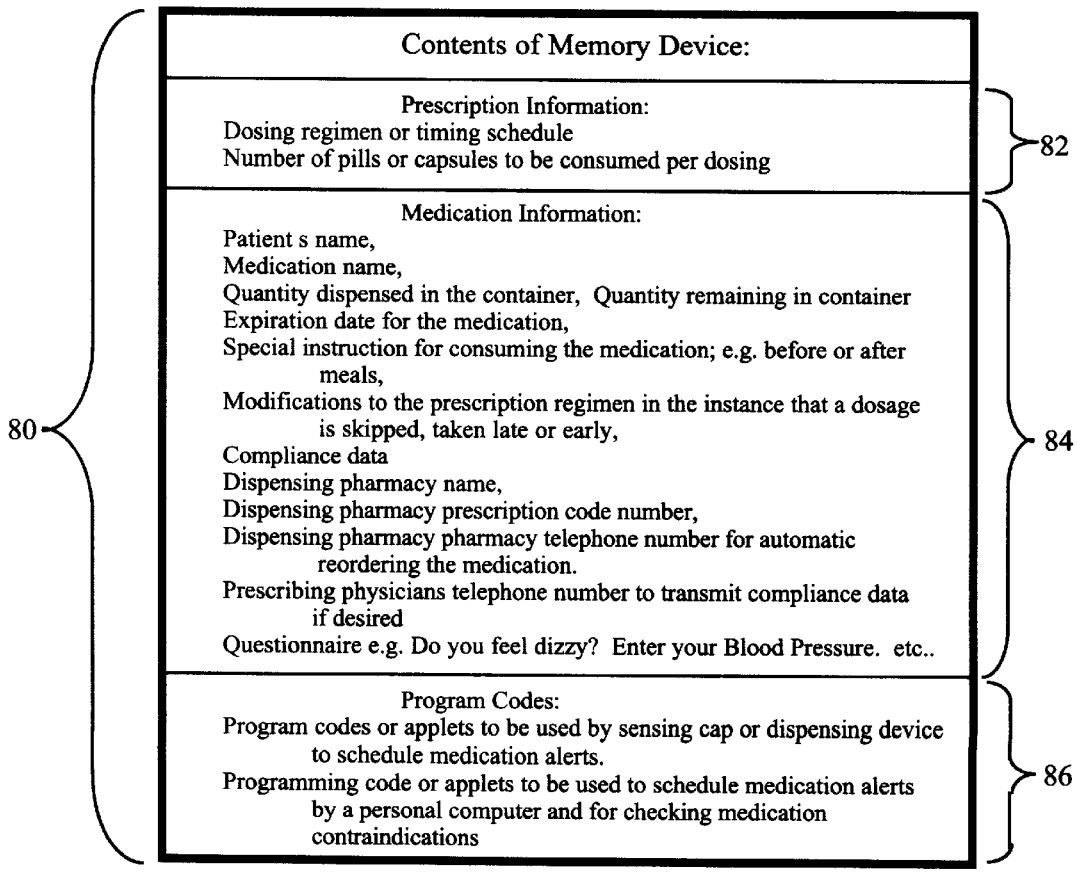
FIG. 8 is a chart listing a variety of prescription information and program codes that can be contained in the memory strip of the interactive label.

As shown in FIG. 8, the memory strip 60 contains a variety of information 80. The contents of the information 80 includes prescription information 82 such as information defining the dosing regimen and the number of pills or capsules to be consumed per dosing. The memory strip 60 also contains medication information 84 and program codes 86 for downloading into or otherwise being sensed or read by the computer processor 120 of the automated cap 100. The electrical contacts 62 and wires 64 communicate with the memory strip 60 so as to access the information 80 in or write additional information to the memory strip. As discussed below, the memory strip 60 can be electronically altered or written to via the processor 120 to store information designating when the cap 100 is removed and reattached to the vial 20, such as removal information 84 indicating that a dose of medication 15 was removed from the vial, quantity information 84 regarding the number of doses remaining in the container, or removal time, disruption or compliance information 84 indicating actual compliance to the prescribed dosing regimen 82. It should be understood that any combination of predetermined information taken from the contents 80 of the memory strip 60 could be communicated to the computer processor 120. The computer processor 120 could use the predetermined information to select or develop desired information for communicating to the patient or care giver.

Figure 7:
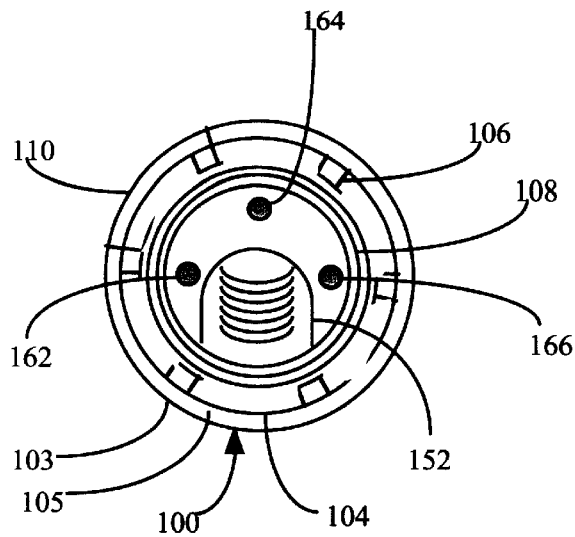
FIG. 7 is a plan view showing the underside of the automated cap used in the first vial-type embodiment of the invention.

As best shown in FIGS. 4, 5 and 7, the cap 100 includes a main body 101 with a top portion 102 and a cylindrical rim 103 having an inside surface 104 and a lower edge 105. The cap 100 includes several hold down lugs 106 and a resilient disc much like those in conventional caps of the type shown in FIG. 1. The hold down lugs 106 are located around the inside surface 104 of the rim 103 near its lower edge 105. The number of hold down lugs 106 coincides with the number of ratchets 40, and the lugs are evenly spaced to align with the ratchets. The resilient disc 108 is attached to the inside surface of the cap 100.

The ratchets 40 interact with the hold down lugs 106 to form a relatively tight, child resistant or childproof seal between the cap 100 and the vial 20. This is accomplished by placing the cap 100 over the open end 25 of the vial 20 so the lugs 106 are aligned directly between the securement ratchets 40. (See FIG. 10). The cap seals the open end 25 of the vial 20 when in this removably aligned position, but the cap is not secured to the vial. The cap 100 is then depressed and rotated clockwise so that each lug slides up the wedge 45 of its corresponding ratchet located to its left, and into a secure position where each lug rests inside the cup 42 of its corresponding ratchet 40. (See FIG. 11). When in this secured position, the resilient disc 108 biases the lugs to remain inside the cups 42 of their corresponding ratchets 40 due to a spring-like force exerted by the resilient disc 108 against the open end 25 of the vial 20. The hold down lugs 106 and ratchets 40 prevent the simple counterclockwise rotation of the cap, and thus its removal. Instead, the cap 100 must be pushed down to compresses the flexible membrane 108, releasing the contact between the lugs 106 and the ratchets 40, before the cap can be rotated counterclockwise.

Figure 6:
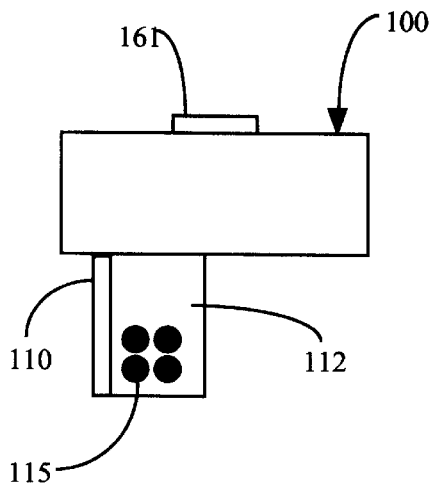
FIG. 6 is an elevation view of the automated cap showing the sensors that engage the electrical contacts of the memory strip.

The automated cap 100 includes a sensing device or sensing tab 110 for sensing the contacts 62 of the memory strip 60. The sensing tab 110 projects down from the edge 105 of the rim 103 of the cap 100. As shown in FIG. 6, the sensing tab 110 has an inside surface 112 with sensors 115. The sensors 115 are positioned to align with the contacts 62 of the memory strip 60 when the cap 100 is in the secured position on the open end 25 of the vial 20. The sensors 115 electrically engage the contacts 62. Predetermined information 80 in the memory strip 60 is electronically transmitted to or otherwise communicated or read by the computer processor 120 via the contacts 62, links 64, sensors 115 and, as discussed below, a circuit board 130.

The sensing tab 110 extends through the opening 31 in the guide ring 30. The opening 31 is sized so that the cap 100 can only be attached to the vial 20 in the one position which aligns the sensors 115 of the sensing tab 110 into electrical engagement with the contacts 62 of the memory strip 60. Specifically, the cap 100 can only be placed on the open end 25 of the vial 20 with the sensing tab 110 abutting or nearly abutting the right end 32 of the guide ring 30. The cap 100 is then rotated in a clockwise direction until the sensing tab 110 abuts or nearly abuts the left end 34 of the guide ring 30 and the hold down lugs 106 have come to rest in the cups 42 of the securement ratchets 40 so that the cap 100 is in its secured position on the vial 20.

Figure 9:
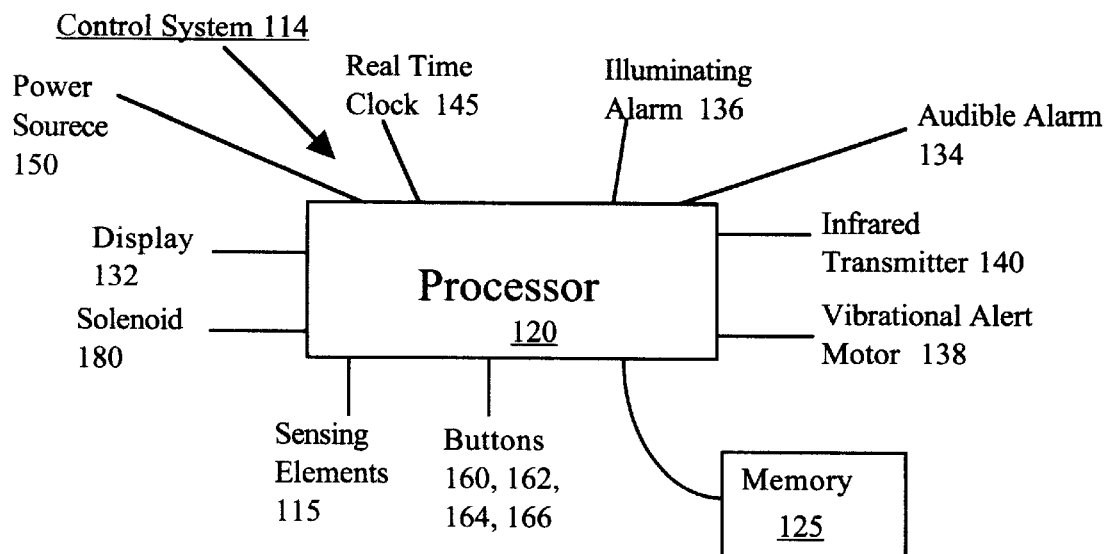
FIG. 9 is a schematic diagram showing the circuitry in the automated cap.

As shown in FIG. 9, the automated cap 100 has a control system 114 that includes a computer processor 120 with its own memory 125. The processor 120 and memory 125 are located on and in electrical communication with a circuit board 130 located inside the cap 100 for protection. (See FIG. 4.) The circuit board 130 electrically connects the processor 120 to a visual communication device such as an LCD display 132. The LCD display 132 visually displays desired information to the patient, such as the date and time the next dose of medication is to be taken and the number of pills to be taken. The display 132 can also indicate an alert or warning to the patient, such as the fact that the patient is so overdue in taking a dose of medication that that dose should no longer be taken. The circuit board 130 also electrically connects the processor 120 to a variety of alarming devices such as audible, visual and vibrational communication devices or alarms 134, 136 and 138, respectively. These alarms 134, 136 and 138 indicate a variety of warnings to a patient, such as when it is time to take a dose of medication. The circuit board 130 also electrically connects the processor 120 to a communication device such as an infrared transmitter 140 that transmits information to or receives information from a separate personal or business computer 270 as discussed below.

As shown in FIGS. 4 and 9, the circuit board 130 is in electrical communication with a battery 150 that powers the processor 120, the display 132, alarms 134, 136, and 138, transmitter 140 and a timing device such as a real time clock 145. An access panel 152 is provided to allow periodic replacement of the battery 150. The access panel 152 is prevented from accidental opening by friction between it and cap 100. In addition, when the cap 100 is secured to the vial 20, the battery access panel 152 cannot slide out due to interference between the wall 22 of the vial 20 and the access panel. Accordingly, the battery 150 should not fall into the medication 15 and accidentally consumed.

The circuit board 130 is in electrical communication with a button 160 for electro-mechanically communicating information to the processor 120. (See FIG. 2). By pressing button 160, the patient is able to send an electrical signal to the processor 120 in response to a question shown on the display 132 or to indicate an action to be taken, such as turn off an alert or alarm. Button 160 is surrounded by a raised ring 161 to protect it from inadvertent contact as it is located on the outside surface of the cap 100. Additional buttons 162, 164 and 166 (see FIG. 7) are located on the inside surface 104 of the cap 100 to enable the patient to set the correct date, hour and minute of the real time clock 145 that is in electrical communication with the processor 120 via the circuit board 130. The computer processor 120 uses the prescribed dosing regimen information 82 and the timing device 145 to calculate or otherwise develop the prescribed times for taking the medication 15. The timing device 145 informs the computer processor 120 when the predetermined times to take the medication occur. The computer processor then informs the patient or individual that it is time to take a dose of medication 15 via the display 132 or an alarm 134, 136 or 138. While buttons 162, 164 and 166 are located on the inside surface 104 of the cap 100, it should be understood that the buttons could be located on the outside surface of the cap as well.

Figure 10:
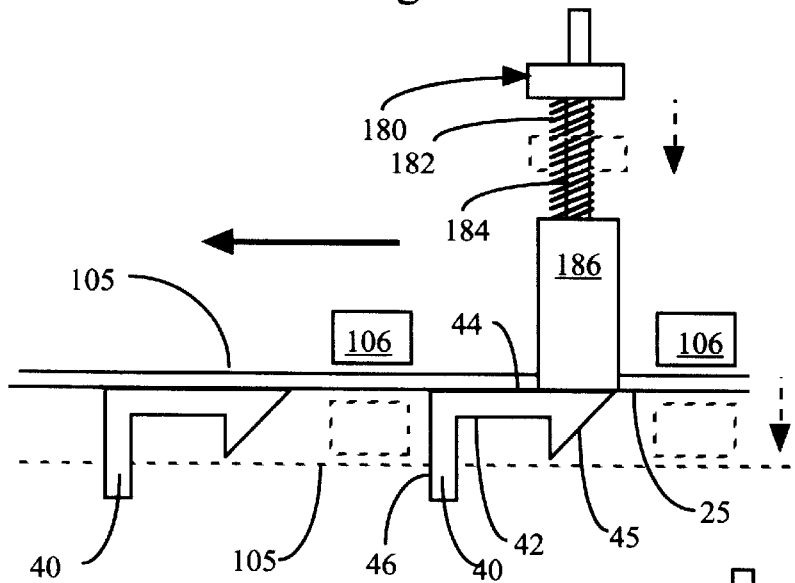
FIG. 10 is an enlarged, diagrammatic view of a portion of the automated cap positioned over the vial, the armature of the locking mechanism of the cap engaging the top of one securement ratchet of the vial, and a pair of hold down lugs of the cap aligned between the securement ratchets of the vial.
Figure 11:
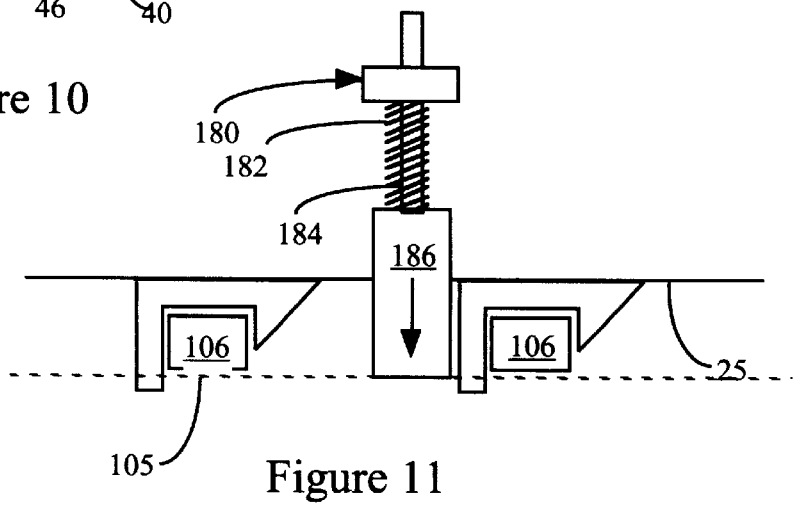
FIG. 11 is an enlarged, diagrammatic view of a portion of the automated cap in a locked position on the vial, the armature of the locking mechanism of the cap received between the securement ratchets of the vial, and the hold down lugs being received in the cup of its respective securement ratchet.
Figure 12:
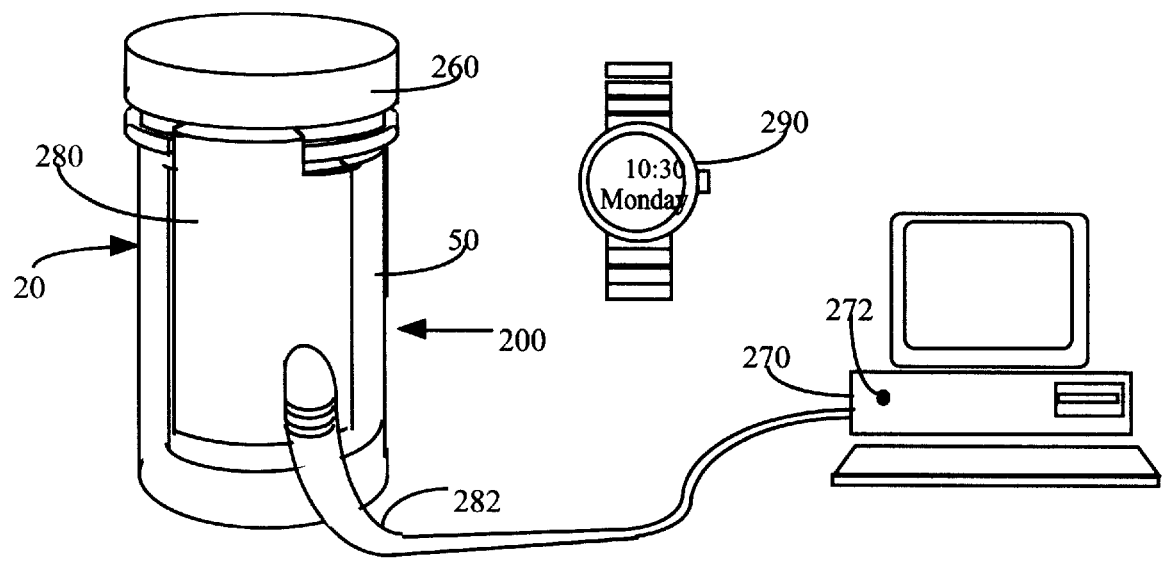
FIG. 12 is a perspective view of a second embodiment of the invention where the medication container includes a conventional, non-automated cap that seals a vial with an interactive label, and a sensing element and cable that conveys information to a separate computer or personal alerting device.
Figure 13:
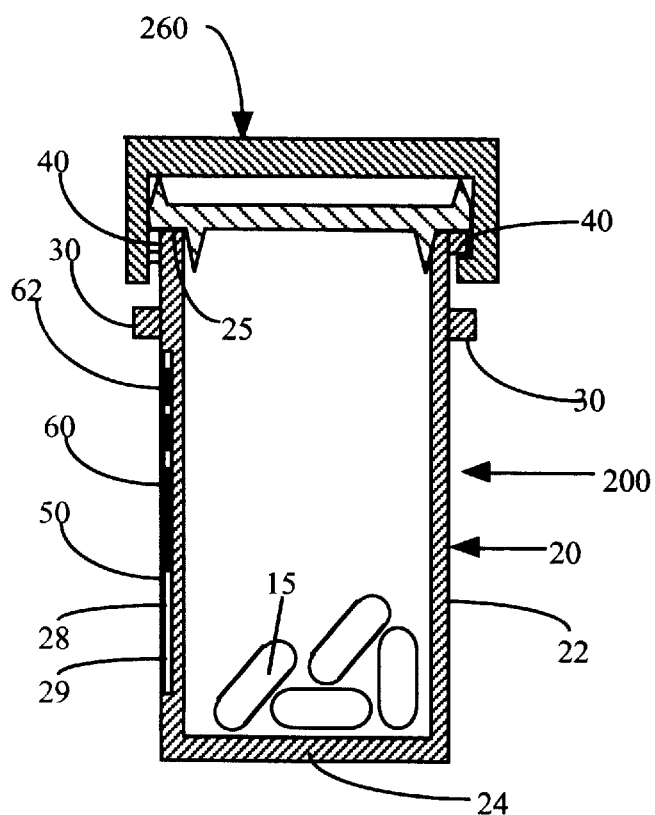
FIG. 13 is a cross-sectional view of a second embodiment of the invention where the medication container includes a cylindrical vial with an interactive label having an electronic memory strip, and a conventional cap.

As shown in FIGS. 9–11, automated cap 100 further includes an access control device formed by the computer processor 120 and a device such as solenoid locking assembly 180 that is in electrical communication with the processor via the circuit board 130. The locking assembly 180 controls the patient's ability to access and remove the medication 15 from the vial 20 until the time the next dose of medication is due according to the prescribed dosing regimen. The assembly 180 includes an armature 182 and a spring 184 for biasing a plunger 186 into a normal, extended position as shown in solid lines in FIGS. 10 and 11. As explained above, to seal the vial 20, the cap 100 is first aligned with open end 25 of the vial so that the hold down lugs 106 are positioned above and in between the ratchets 40 of the vial. (See FIG. 10). The cap 100 is then depressed into a removably aligned position over the open end 25 so that the lugs 106 move directly between the ratchets 40. The plunger 186 contacts the upper surface 44 of the ratchet 40 which causes spring 182 to compress. This is shown in FIG. 10 in phantom lines. The cap 100 is then rotated clockwise into its secured position where each hold down lug 106 rests in the cup 42 of its respective ratchet 40. When in this secured position, plunger 186 clears the side 46 of the ratchet 40 so that spring 184 biases the plunger into its normal, extended position. Attempts to remove the cap 100 by rotating it counterclockwise are resisted by plunger 186 which abuts the side 46 of the ratchet 40. The cap 100 is now locked into its secured position. The processor 120 is programmed to activate the solenoid locking assembly 180 to draw up the armature 182 and plunger 186 when the next medication dosage is due to be taken. Only then can the cap 100 be rotated counterclockwise and removed.

Second Embodiment of Circuitry

The control system 114 shown in FIG. 9 has the processor 120 located in the cap 100. This arrangement is based on the advantage of being able to dispose of the vial 20 when the medication 10 is used up, and the information in the memory strip 60 has been transferred to another data base, such as the memory of a patient's home computer or a pharmacy, hospital or prescribing physician computer. The more expensive cap 100 is retained by the patient for further use. However, ongoing manufacturing developments continue to reduce the costs of producing memory devices with their own processors. As a result, the cost of producing the memory strip 60 is not significantly different than the cost of producing the memory strip together with its own processor.

Figure 25:
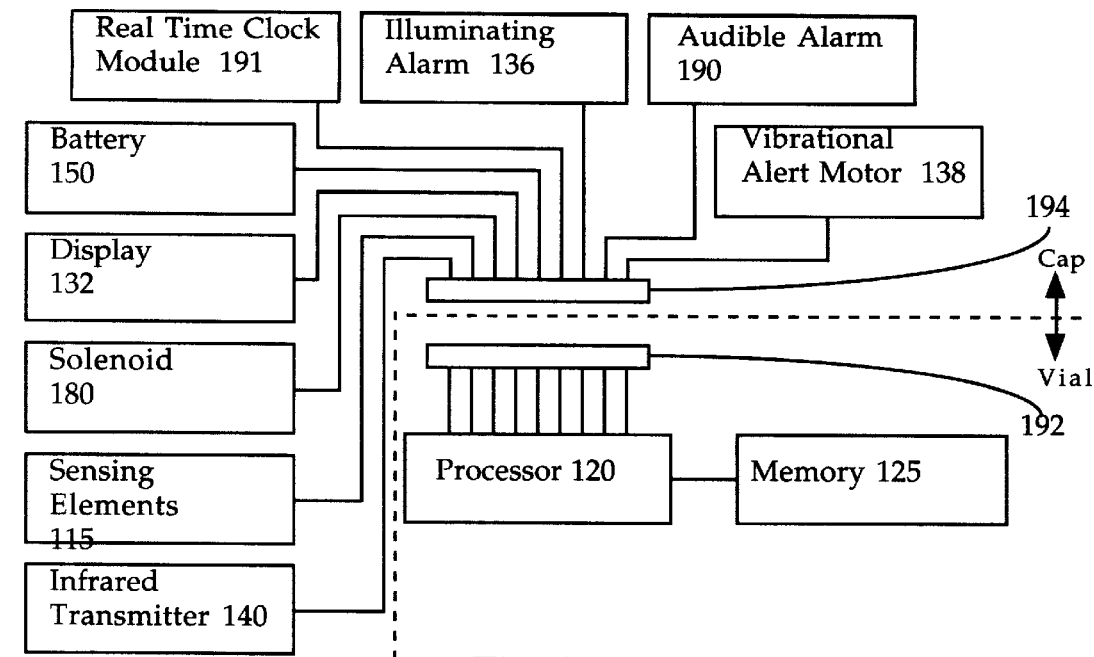
FIG. 25 is a schematic drawing of an alternate circuitry to FIG. 9 where both the computer processor and memory strip are affixed to the vial or blister pack, and the other hardware components are contained in the cap or lid.

FIG. 25 shows an alternate control system 190 where the memory strip 60 has its own processor 120. Both the memory strip 60 and processor are secured to the wall 22 of the vial 20. The memory strip 60 is directly wired to the processor 120 and serves as the memory of the processor. The memory device 125 in the cap 100 is eliminated. This saves the costs associated with producing two separate memory devices, without compromising the disposability of the vial 20. Hardware components such as the circuit board 130, display 132, alarms 134, 136 and 138, transmitter 140, battery 150 and solenoid 180 remain in the reusable cap 100. The real time clock 145 is replaced by a real time clock module 191 that is capable of maintaining time without being connected to the processor 120. The components in the cap 100 are electrically connected to the processor 120 via multiple contacts 192 and 194. Multiple contact 192 is wired to the processor 120 and replaces contacts 62. Multiple contact 194 is wired to the circuit board 130 and secured to the inside surface 112 of sensing tab 110 and replaces sensor 115. The alignment of the multiple contacts 192 and 194 is achieved in the same manner as the alignment of the contacts 62 and sensor 115.

Operation of First Embodiment

When the automated cap 100 is secured to the medication vial 20, the control system 114 is complete. The sensors 115 on the tab 110 of the cap are in electrical contact with the contacts 62 of the memory strip 60, and the information 80 in the memory strip is in electrical communication with or can otherwise be read by the processor 120 in the cap. Predetermined portions of information 80 from the memory strip 60 are compared with the information that had previously been read and stored in the memory 125 of the cap 100. If the predetermined information 80 is the same as before, the processor 120 will compute the next prescribed time for taking a dosage of medication 15 and activate an alarm or otherwise communicate that information to the patient when that time occurs. If the cap is not returned to seal the vial 20 to which it was previously attached, the audible alarm 134 will be activated by the computer 120. The patient or care giver can disable the alarm 134 by securing the cap 100 back on the correct vial 20. If the cap 100 is not returned to the correct vial 20 and the alarm 134 is ignored for a period of time or the user presses button 160, the alarm is disabled, and the new information 80 in the new memory strip 60 is stored in the memory 125 of the cap 100 and used to compute the next dosage time for the new medication. The automated cap 100 will keep an accurate count of the number of times the medication container is opened each day and advise the patient against consuming too many pills in too short a time. This is particularly useful for medications 15 that are prescribed to be used on an as needed basis (e.g. pain medication), but not to be consumed more than a certain amount in any given day.

When the automated cap 100 is removed, it can no longer read the memory strip 60. This triggers an event that can be used to store the current date and time in memory 125 of the cap 100. When the cap 100 is resecured to the vial 20, the date and time are written to memory 125 or to the memory strip 60 indicating that the patient took a dose of medication 15 and the actual consumption time. The times and dates stored reflect consumption compliance information or compliance data in adhering to the prescription regimen. The actual compliance data 84 can be conveyed to a separate personal or business computer 270 via an interface in the computer (not shown) that can sense a controlled flashing of the illuminating alarm 136. By pressing button 160 for a period of several seconds the automated cap 100 will transmit the compliance data 84. The compliance data 84 may also be conveyed via the infrared transmitter 140 in the automated cap 100 to an infrared receiver 272 in the computer 270. The compliance data 84 is used by the physician to determining if the patient is taking too much or not enough medication 15, or is not adhering to the regular timing specified by the prescription.

By comparing the quantity of medication 15 in the container 10, as stored as medication information 84 in the memory strip 60, against the number of times the automated cap 100 was removed and the number of pills to be consumed in each dosage, the automated cap 100 can compute the inventory of medication in the container 10, when the prescription should be refilled and alert the patient. The number of times the container 10 is opened and the numbers of doses consumed is written to the memory 125 of the cap 100 or the memory strip 60 of the interactive label 50.

As stated above, the information 80 contained in the memory strip 60 can be transmitted to a separate personal or business computer 270 or personal alerting device 290, such as a digital watch or appointment book, by equipping automated cap 100 with an infrared transmitter 140. The transmission is started by pressing button 160 for several seconds. The transferred information is used to establish an alert timing schedule 82 to remind the patient when to take the medication 15. This is accomplished by having the computer 270 activate a variety of its alarms, or by having the computer page the patient with a message to consume a specific medication, or by calling the patient using a telephone to convey a verbal message to consume a specific medication. In this manner, the patient can extend the alarm and alerting devices beyond what is available in the cap 100, or to have alerts be issued even if a conventional cap is used.

If a patient is taking several medications 15 and the information 80 contained in the memory strip 60 for each container 10 is transferred to a separate personal or business computer 270, the computer can reference and compare the lists of contraindicated medications which are part of the medication information 84. Should two or more medications 15 be contraindicated for use together, the patient will be alerted to this fact. Every time a medication 15 is issued to a patient, the most recent list of contraindications is included in the memory strip 60 of the container 10. If the patient does not have a software program capable of performing this function, the program codes 86 will contain a program that is transferred from the memory strip 60 to the computer 270 to perform this check. This program may use a Java programming language so that it can be used in a wide variety of computer processors 270. Other program codes 86 can be sent to the automated cap 100 or computer 270 to perform various alerting functions.

Second Embodiment

FIGS. 12–15 show a second embodiment of the invention where the container 200 includes a conventional, childproof cap 260 as shown in FIG. 1, in place of the automated cap 100. The vial and interactive label that are interchangeable with the vial 20 and label 50 of the first embodiment. The interactive label 50 is electrically linked to the separate personal or business computer 270 via a sensing element 280. The conventional cap 260 is secured to the vial 20 via securement ratchets 40 as in the first embodiment. The guide ring 30 is located a predetermined distance from the top end 25 of the vial 20 so that the ring does not interfere with securing the conventional cap 260 to the vial 20.

The information 80 contained in the memory strip 60 is electronically conveyed to computer 270 by sensing element 280. Sensing element 280 has sensors 281 located on its inside surface in a pattern and position similar to the contacts 62 of the memory strip 60. The sensing element 280 has an arcuate shape to matingly engage the cylindrical wall 22 of the vial 20 so that when the sensing element is aligned with and placed over the interactive label 50 its sensors 281 are in electrical contact with the contacts 62 of the memory strip 60. The sensing element 280 includes a connecting cable 282 with an electronic connector 284 adapted to be plugged into or otherwise electrically communicate with the computer 270. Sensing element 280 has an upper tab sized to fit snugly into the opening 31 between the ends 32 and 34 of the guide ring 30. This can be accomplished when the conventional cap 260 is in place as shown in FIG. 11. It should also be understood that the sensing element 280 can be used to transfer predetermined information 80 to or from the memory strip 60 of either the first or second embodiment of the container 10 or 200 to the computer 270. When the sensing element 280 is used with the first embodiment, the automated cap 100 must be removed.

Third Embodiment

FIGS. 16 and 17 show a third embodiment of the invention where the container 300 includes a modified interactive label 350 and an automated cap 370 with a modified sensing tab 372. Cap 370 is otherwise interchangeable with cap 100. The container 300 includes a vial that is interchangeable with the vial 20 in the first embodiment. The label 350 includes two rows of conductive or non-conductive contacts 352 and 354. These contacts 352 and 354 can also take the form of reflective or non-reflective surfaces. These contacts or surfaces 352 and 354 represent 1s and 0s. The contacts or surfaces 352 and 354 combine to form a code representing the prescription regimen.

The inside surface of downwardly projecting sensing tab 372 includes sensors 374 that detect the presence or absence of a conductive or reflective surface 352. When the surfaces are conductive, one of the conductive surfaces 352 acts as a ground surface 356 for the remaining surfaces 352. By detecting a voltage or current between the ground 356 and any of the other conductive surfaces 352 a bit of information may be read as a 1 or a 0. By combining the bits of information together, a binary number may be created that can represent a prescription information 202.

In FIG. 16, there are a total of ten contacts or surfaces 352 and 354. One contact or surface is the ground 356. Another second contact or surface 358 is used to sense when the cap 370 is removed. Of the eight remaining contacts or surfaces 352 and 354, two are used to indicate the dosage, for example a 0 may represent one pill, a 1 to indicate two pills and a 2 to represent three pills, and a 3 to indicate four pills are to be taken as each dosage. The remaining six contacts or surfaces are combined to represent a number between 0 and 63. These surfaces 352 and 354 are used to represent the timing of the prescription regimen, 0 to represent a dosage every 2 hours, a 1 to indicate a dosage every 3 hours, a 2 to indicate a dosage every 4 hours and so on. While ten surfaces are shown and described, it should be understood that more or fewer may be used.

The conductive or reflective surfaces 352 may be part of a larger conductive or reflective surface (not shown). A non-conductive or non-reflective surface 344 may be created by punching a hole in or printing over a portion of the larger conductive or reflective surface. This process may be done as the label 350 is printed with the readable text 44.

The automated cap 370 is secured to the vial 20 the same way as in the first embodiment. The cap 370 includes the same processor 120, memory 125, circuit board 130, display 132, alarms 134–138, transmitter 140, clock 145, battery 150 and buttons 160–166 as automated cap 100. When the cap 370 is removed from the vial 20, the conductive path between ground surface 356 and second surfaces 358 is broken indicating to the cap 370 that a dosage of the medication is being taken. The braking of this conductive path is also used to set the alarms to indicate when the next dosage should be taken.

Fourth Embodiment

FIGS. 18–24 show a fourth embodiment of the invention where the container 400 is a single dosage, disk shaped, blister pack and an interactive label 450 with a memory strip 460. The blister pack 400 is placed in a dispenser 500 having a computer processor 530 that controls a display and a variety of alarms. Memory strip 460 is functionally and structurally substantially interchangeable with memory strip 60. It should be understood that in this embodiment of the invention, the dispenser 500 forms a part or piece of the container 400.

Figure 18:
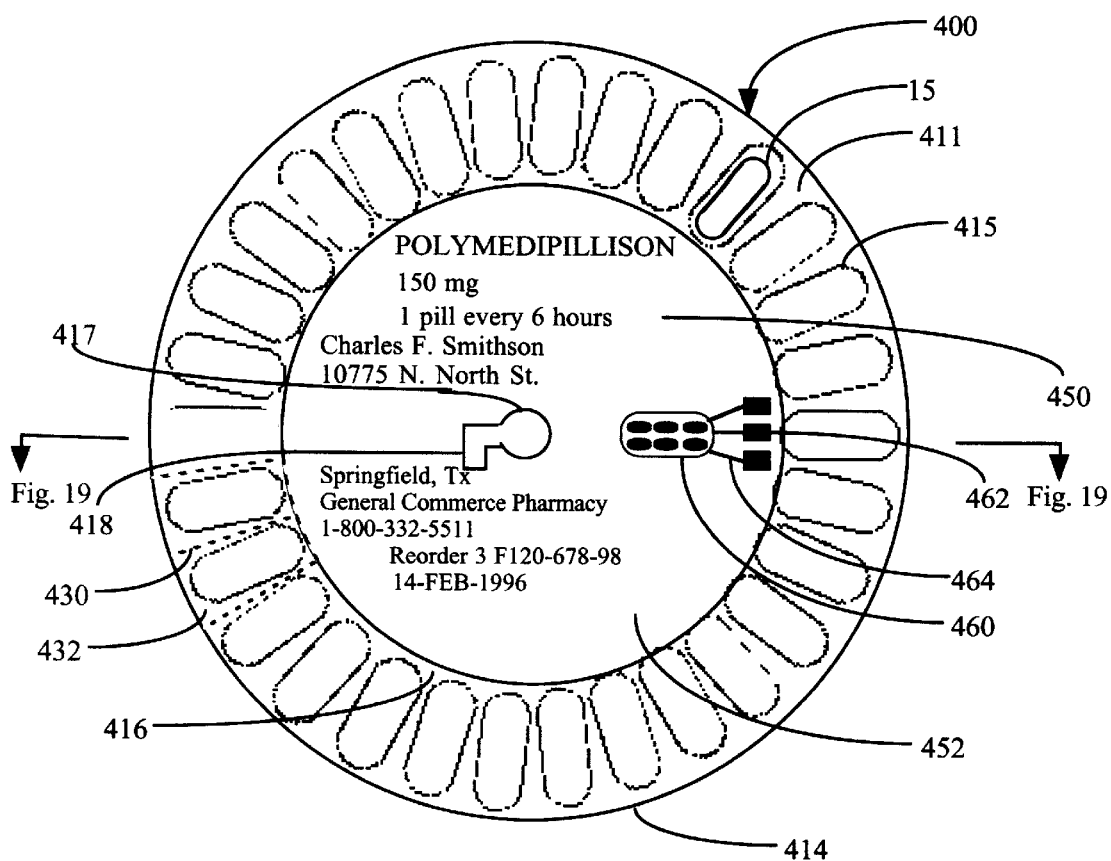
FIG. 18 is a top, plan view of a fourth embodiment of the present invention where the medication container is a disc shaped blister pack with an interactive label having an electronic memory strip affixed to a central surface of the blister pack.
Figure 19:
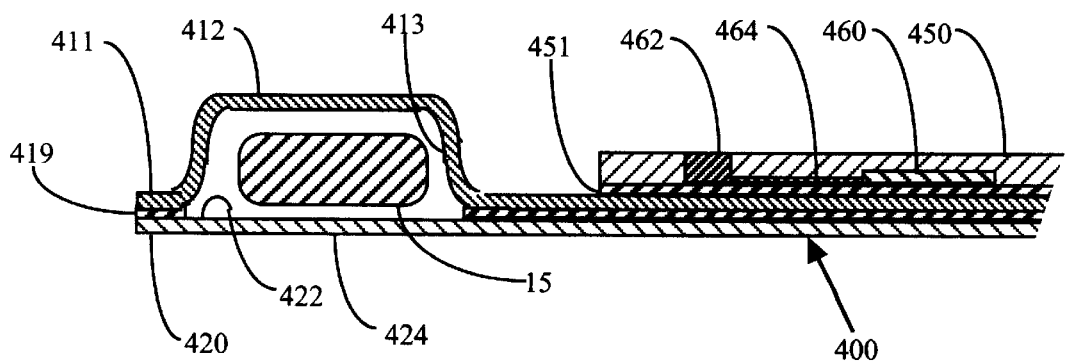
FIG. 19 is a side, cross sectional view of FIG. 18 taken along line 19—19 showing a dose of medication in a pocket of the blister back and the interactive label affixed to the tear resistant sheet.
Figure 20:
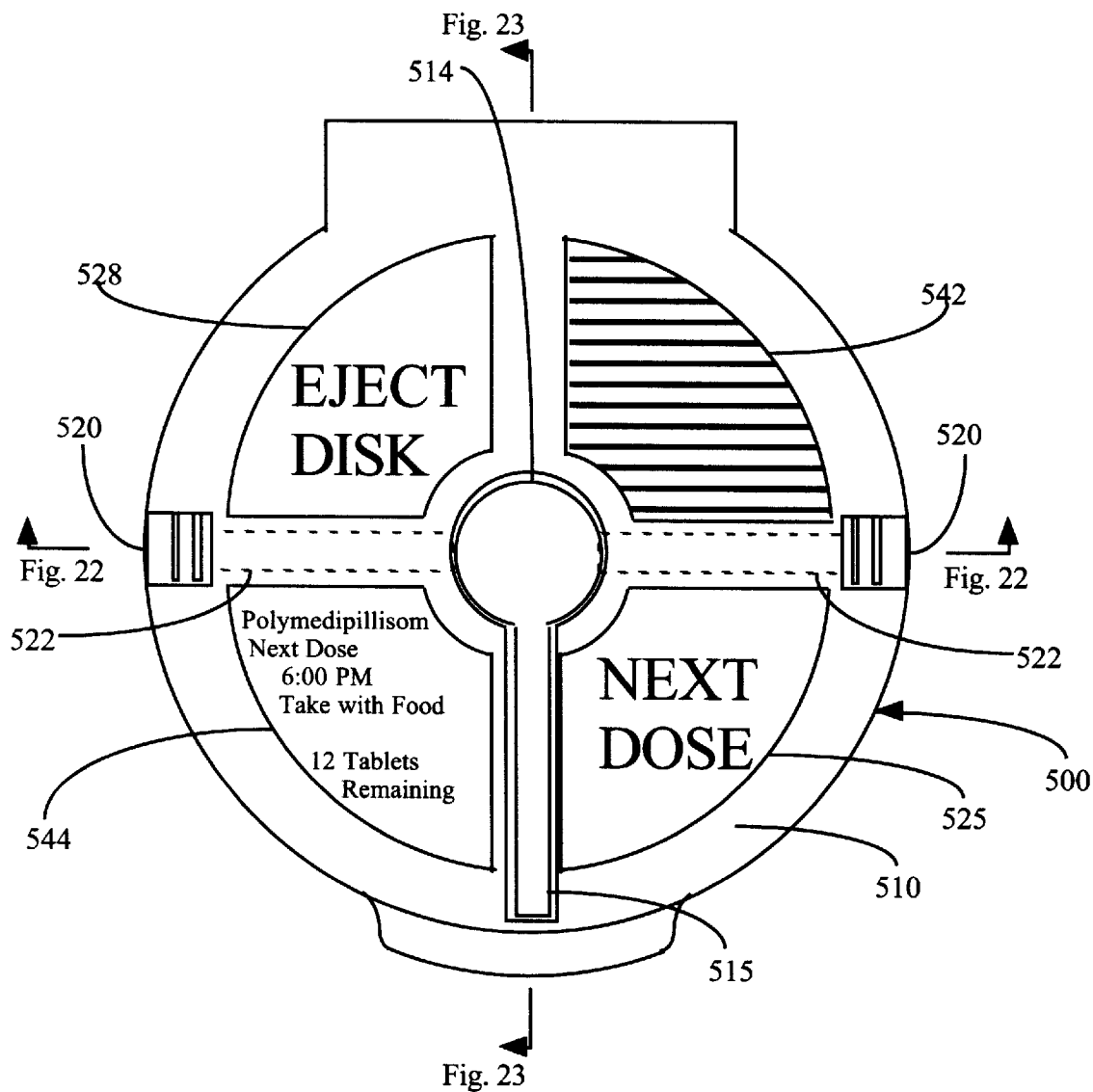
FIG. 20 is a top, plan view showing the lid of a semi-automated dispenser equipped with a dispensing lever, finger latches, a display, an audible alert, "Eject" and "Next Dose" buttons.
Figure 21:
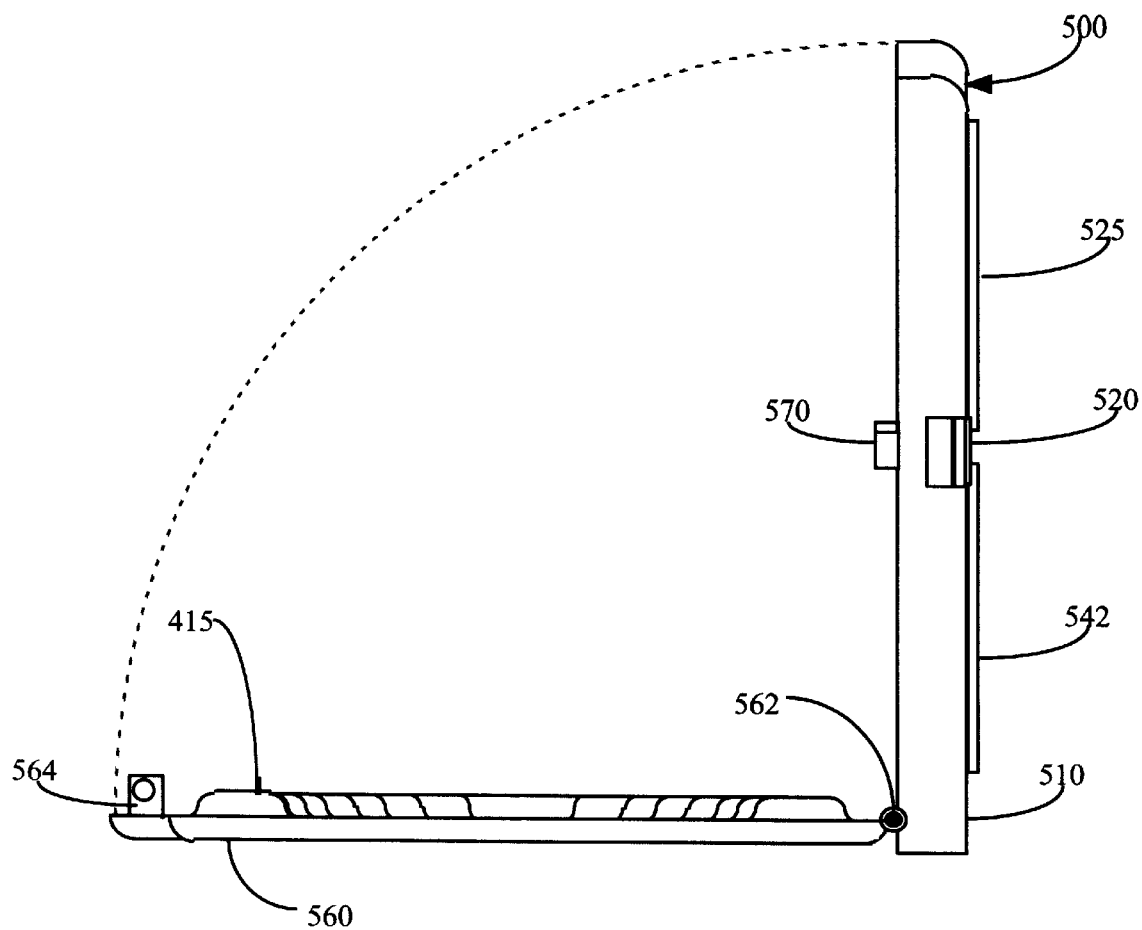
FIG. 21 is a side, plane view showing the disc shaped blister pack inside a semi-automated dispenser in an opened position.
Figure 22:
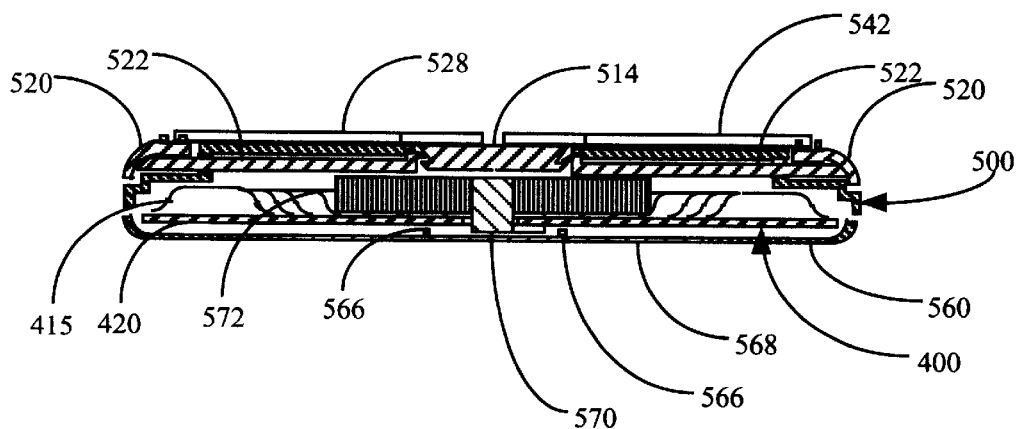
FIG. 22 is a side, cross-sectional view of FIG. 20 taken along lines 22—22 and showing the semi-automated dispenser with its plunger in a locked position.

FIGS. 18 and 19 show a blister pack 400 formed by a tear resistant sheet 411 having front and rear surfaces 412 and 413 and a perimeter 414. The tear resistant sheet 411 is formed into multiple pockets 415 located around its perimeter 414. Each pocket 415 holds a single dose of medication 15. The tear resistant sheet 411 has a substantially flat central area 416 with a central opening 417 and offset notch 418 formed through the sheet 411. The rear surface 413 of the tear resistant sheet 411 has an adhesive coating 419 applied to it, except in pockets 415. The blister pack also includes a backing sheet 420 having front and rear surfaces 422 and 424. The front surface 422 is secured to the rear surface 413 of the tear resistant sheet 411 via the adhesive coating 419. The backing sheet 420 extends over the pockets 415 so that each doses of medication 15 is sealed into its respective pocket. The tear resistant sheet 411 has perforations 430 that separate each pocket 415 into a discrete portion 432 that is separable from the remainder of the container.

An interactive label 450 is attached to the flat, central area 416 of the front surface 412 of the tear resistant sheet 411 via an adhesive layer 451. The label 450 has a textual portion 452 with prescription information printed on its front surface. The label 450 includes a memory strip 460 similar to that used in the first and second embodiments. The information in the memory strip 460 is the same as the information 80 in the first and second embodiments. The electronic memory strip 460 is sensed through its contacts 462 via an electrical connection or wire 464. The opening 417 and notch 418 in blister pack 400 are used to mount the single dosage container 400 into a predetermined position in the dispensing device 500. The opening 417 and notch 418 ensure that the blister pack 400 is placed in a secure position in said dispenser 500, and that the sensing contacts 462 are aligned with sensors for electrically communicating with the memory strip 460.

Figure 23:
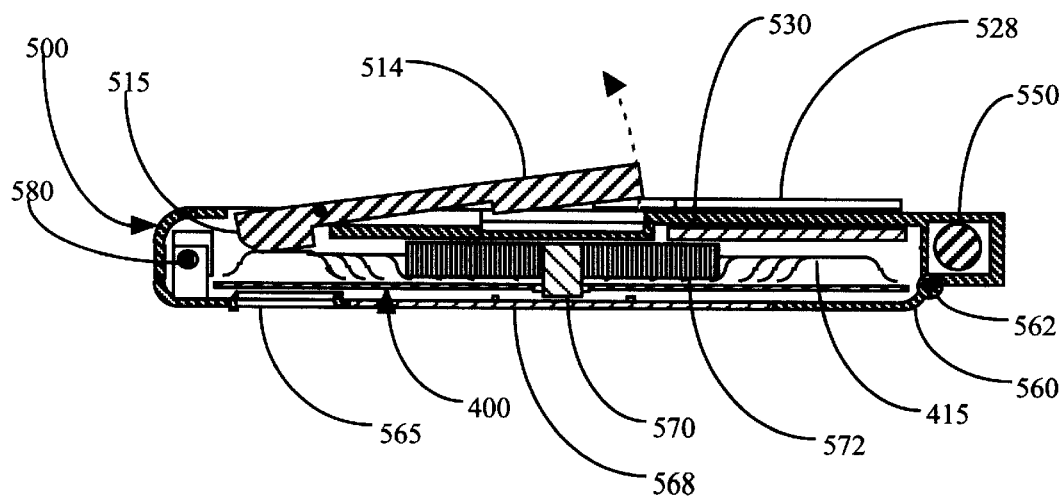
FIG. 23 is a side, cross-sectional view of FIG. 20 taken along lines 23—23 and showing the semi-automated dispenser with its plunger being raised into a dispensing position.

FIGS. 20–23 show the semi-automated, clam shell medication dispenser 500 for housing and dispensing medication 15 from the blister pack container 400. The dispenser 500 has a lid 510 with a dispensing lever 514 and a plunger 515 that combine to form a dispensing mechanism for dislodging a dose of medication 15 from its pocket 415 in the blister pack 400. Finger latches 520 are arranged on both sides of the dispensing lever 514 and plunger 515. The latches 520 are integrally connected to locking struts 522 which engage the dispensing lever 514. (See FIG. 20). To dispense a dose of medication 15, the patient pushes each finger latch 520 out and away from the body of the lid 510 so that struts 522 release the dispensing lever 514. When released, dispensing lever 514 is biased by a spring (not shown) to a raised position above the struts 522 as seen in FIG. 23. When the finger latches 520 are released, the latches and struts 522 are biased by a second spring (not shown) into their original position. The struts 522 are now located beneath the dispensing lever 514. This structure is intended to provide a relatively child-proof or resistant method for releasing dispenser lever 514.

The dispenser 500 is now ready to dispense medication 15. The lever 514 is pulled up, which causes dispensing plunger 515 to rotate down and press against the top of the blister pack pocket 415 positioned below the plunger. As the plunger continues to rotate down, the medication 15 is forced through backing sheet 420 of the single dose container 400 and through a dispenser opening 565 for the patient to consume. The predetermined information 80 in the memory strip 460 is downloaded to or sensed by the processor 530 of the dispenser 500 via a sensing mechanism (not shown) attached to the lid 510. The sensing mechanism has sensors similar to those in sensing tab 110. These sensors engage the contacts 462 of the memory strip 460. The computer processor 530 has circuitry similar to that shown in FIG. 9 and includes a memory and a real time clock that are electrically connected via a circuit board. Information 80 in the memory strip 460 is electronically transmitted to or otherwise communicated or read by the computer processor 530 via the contacts 462, links 464, sensors and the circuit board. The lid 510 also includes a "Next Dose" button 525 for advancing the single dosage container 400 to the next dosage position, and an "Eject" button 528 for ejecting the container 400. Communication devices such as audible alerting device 542 and display 544 are used to present messages and visual alerts. These buttons 525 and 528 and communication devices 542 and 544 are in electrical communication with the computer processor 530 via the circuit board.

Figure 24:
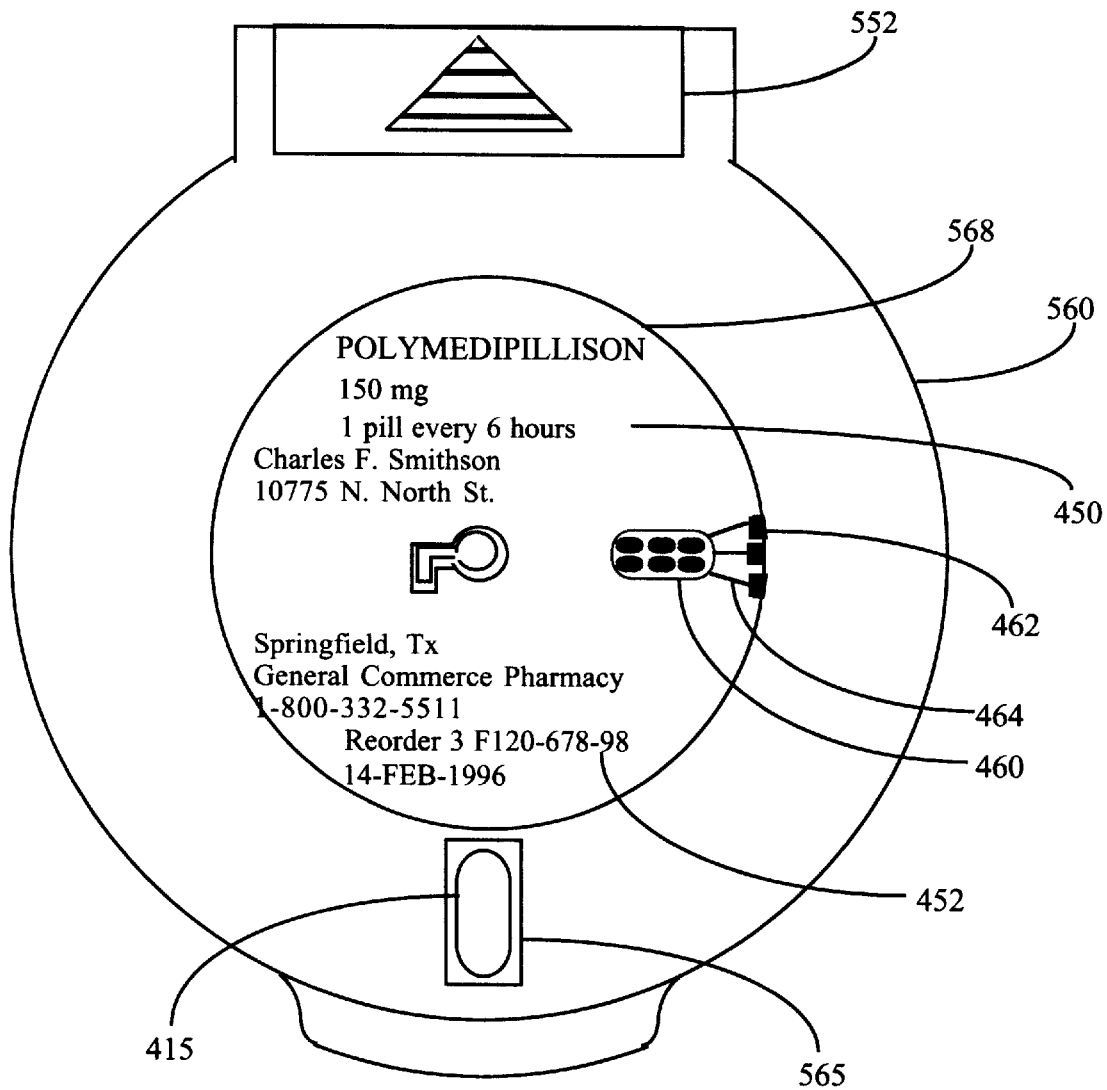
FIG. 24 is a bottom, plan view of the dispenser showing an alternate embodiment of the blister pack container where the interactive label is secured to the backing sheet of the blister pack so that the textual portion of the label is visible through a window in the base of the dispenser.

The dispenser 500 has a base 560 that is hingably attached to the lid 510 by hinge 562. The base 560 includes a battery 550 for powering the electrical components in the dispenser, and a battery access door 552 to permit periodic replacement of the battery. The base 560 has a dispenser opening 565 through which the backing sheet 420 of one of the discrete portions 432 of the blister pack 400 can be seen, and through which individual doses of medication 15 are dispensed. To assist in breaking or tearing the backing sheet 408, a portion of the dispenser opening 565 has a sharp interior edge that cuts into the surface of the backing sheet 420 as the sheet is pressed against the edge. The base 560 of the dispenser 500 also includes a flange 564 that secures the lid 510 to the base 560 when in the closed position. Alignment ribs 566 project upwardly from the inside surface of the base 560 to keep single dosage container 400 adequately raised so a drive spindle 570 passes through the central opening 417 in the tear resistant sheet 411 when the dispenser 500 is closed. The alignment ribs 566 and the shape of the spindle 570, which matingly engages the central opening 417 and offset notch 418 of the blister pack 400, combine to form a mechanism for selectively aligning one of the pockets 415 with the plunger 515 of the dispenser. FIG. 24 shows an alternate embodiment of the blister pack container 400. In this embodiment, the interactive label 450 is affixed to the surface of the backing sheet 420. A window 568 made of clear plastic is provided in the base 560 of the dispenser 500. The window 568 allows the patient to read the contents of the prescription text 452 when the dispenser is closed.

The dispenser 500 is equipped with a drive spindle 570 and a motor 572 for automatically dispensing the medication 15. The motor 572 is relatively flat in design similar to those used in portable CD players. The computer processor 530, motor 572 and spindle 570 combine to form an access control device or advancing mechanism for rotating the single dosage container 400 when a dose is to be dispensed. The computer processor 530 controls the activation of the motor 572 and spindle 570 to prevent the patient or care giver from removing medication 15 from the blister pack 400 until the time the next dose of medication is due. The motor 572 also controls a locking solenoid 580 that prevents inappropriate access to the medication container 400 by the patient or care giver. The solenoid 580 controls a rod aligned to selectively engage or enter an opening in flange 564. When the solenoid 580 is activated to force the rod into the latch opening, the dispenser 500 is locked shut. When the solenoid 580 is activated to pull the rod out of the latch opening the dispenser 500 can be opened.

Operation of Fourth Embodiment and Dispenser

To use the personal semi-automated medication dispenser 500, the patient can press the "Eject" button 528 and insert a full blister pack container 400. Processor 530 causes the single dosage container 400 to rotate via motor 472 such that the contacts 462 of the memory strip 460 are below the sensors of the dispenser 500 (not shown) which are in electrical communication with the computer processor 530 via the circuit board. When properly positioned the processor 530 may write to the memory strip 460 to update it with the number of doses that have been dispensed, so the quantity of medication 15 stored in memory strip 460 is accurate. When all the medication 15 is dispensed, the computer processor 530 is programmed to accept input from the "Eject" button 528. The computer processor 530 then causes locking solenoid 580 to retract and allow hinged lid 510 to open under spring force. The existing single dosage container 400 is removed and a new one placed so that center opening 417 is pressed over drive spindle 570. The hinged top 550 is closed, causing the locking solenoid 580 to engage the opening in flange 564 and locking the dispenser closed.

The information 80 in the memory strip 460 is transferred to processor 530 so that the prescription regimen is shown on the display 544. When it is time to take a medication 15, the processor causes audible alarm 542 to sound an alert. The patient then presses the "Next Dose" button 525. Processor 530 causes motor 572 to rotate the spindle 570 and single dosage container 400 to the next available filled pocket 415. The patient then releases the dispensing lever 514, as previously described, and lifts the lever up to dispense a dose of medication 15. When this is done a micro switch or sensor (not shown) detects the dispensing of a dose of medication 15 and reduces the quantity of medication understood by the processor 530 to be held in container 400 by one. The dispensing lever 514 is then secured into its lowered position. It should be noted that the dispensing lever 514 could be adapted to engage the blister pack 400 near perforations 430 to separate an entire discrete portion 432 from the remainder of the blister pack while leaving the medication 15 inside its discrete portion. The discrete portion 432 of the blister pack 400 would then be discharged through opening 565 in the dispenser 500 so that the patient could remove the medication from the discrete portion themselves.

As previously described portions of the information 80 in the memory strip 460 can be transferred to the separate computer 270 or personal alerting device 290. Program codes 86 can be transferred so computer 270 is equipped with software to provide alert scheduling or to check for contra-indicated medications. Program codes 86 can be transferred to processor 530 of dispenser 500 to assist in scheduling alerts. Additional buttons (not shown) are used to enter the date and time. The dispenser can also be provided with other alarms (not shown) such as a visual or vibrational alarm, an infrared transmitter (not shown) for communicating with a separate computer, and connectors (not shown) for electrically attaching the dispenser to the separate computer 270.

Fifth Embodiment

Figure 26:
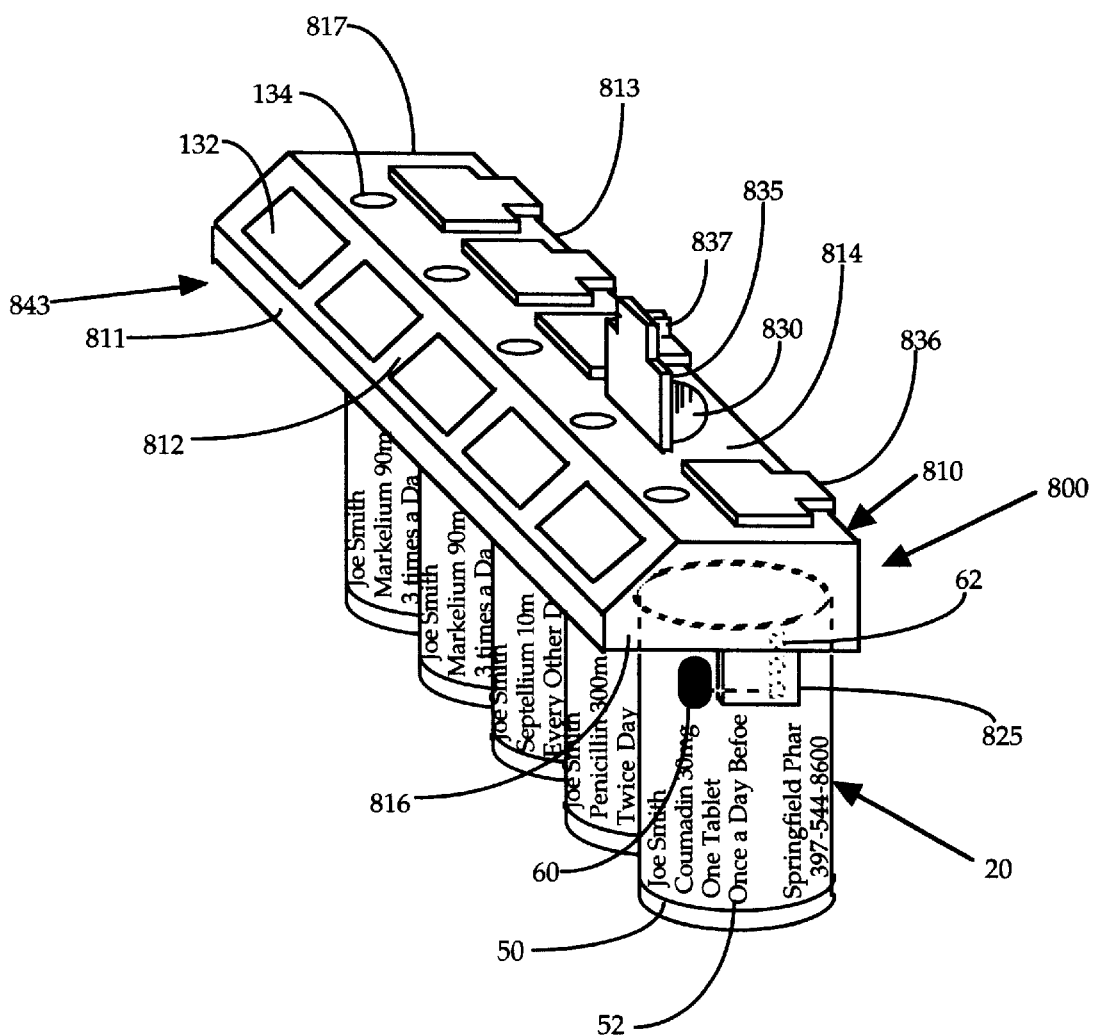
FIG. 26 is a perspective view of a fifth embodiment of the present invention where the medication container includes several vials of medication secured to a unitary lid, each vial having its own machine readable information strip, and the lid having a separate indicator light, display and access door for each vial.

FIG. 26 shows a fifth embodiment of the medication container 800 for holding and organizing several different types of medication. The container 800 includes several vials that are the same as or similar to the vials 20 for containers 10, 200 and 300. Each particular vial 20 is physically separable from the other vials, but is removably secured to a unitary lid 810 as discussed below. Each particular vial 20 is equipped with its own corresponding interactive label 50 and machine readable and writable memory strip 60. However, it should be understood that in this embodiment of the invention, the label 50 need not be interactive. The machine readable and writable memory strip 60 can be replaced by a memory device that is only machine readable. For example, memory strip 60 and its contacts 62 and wires 64 can be replaced by the several conductive/non-conductive or reflective/non-reflective surfaces and ground surface 352-358 of container 300, or by a conventional bar code (not shown) applied to the surface of the label 50.

Figure 27:
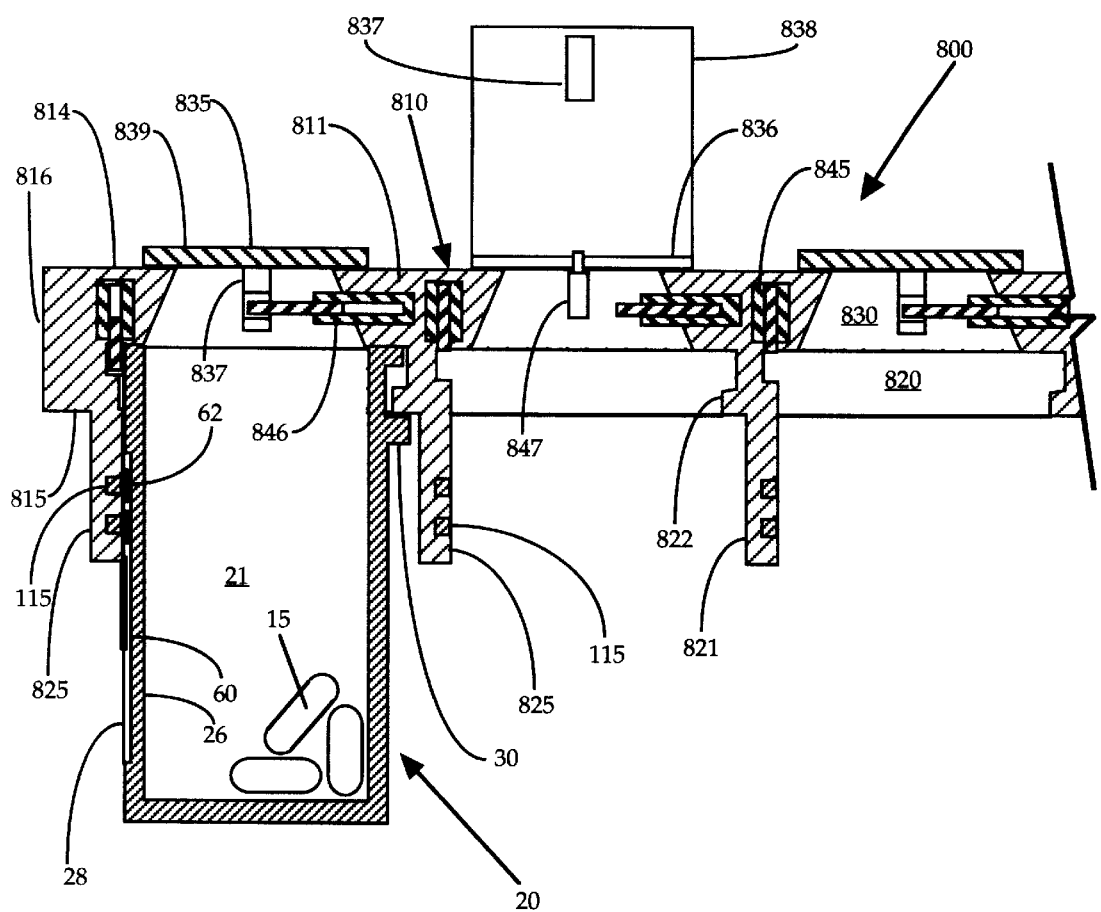
FIG. 27 is a partial, rear cross-sectional view of the multi-vial medication container of FIG. 26 with one vial secured to an associated porthole of the unitary lid and adjacent access doors in their open and closed positions.

The unitary lid 810 includes a housing 811 with front 812, rear 813, top 814, bottom 815, and end surfaces 816 and 817. As shown in FIG. 27, a number of ports or portholes 820 are formed along the length of the bottom surface 815. The portholes 820 are spaced equidistantly apart from one end 816 of the housing to the other 817. Each porthole 820 has an inside surface 821 that is shaped and sized to snugly receive the top end 25 and ratchets 40 of one of the vials 20. Similar to the cap 100, the inside surface 821 of each porthole 820 includes several hold down lugs 822 or threads for removably securing the vial 20 to the unitary lid 810. Each particular port 820 has a corresponding sensing tab 825 that includes sensors 115 like those in cap 100. The sensing tabs 825 projects downwardly from the bottom surface 815 of the lid 810 and have an inside surface that is substantially flush with the inside surface 821 of the porthole 820.

Each vial 20 has a guide ring (not shown) similar to guide ring 30 that receives the sensing tab 825. The label 50 is affixed in the recess 28 of the vial 20. The recess 28, guide ring 30 and sensing tab 825 combine to align the textual portion 52 facing toward the front 812 of the unitary lid 810 when the vial is secured. This ensures that each textual portion 52 is visible when several vials 20 are secured to the unitary lid 810. The guide rings 30 also ensure that sensors 826 align with contacts 62 in control system 840 (FIG. 28), or that contacts 192 align with contacts 194 in control system 190 (FIG. 25).

The housing 811 of the unitary lid 810 has a number of openings 830 in its top surface 814. Each of these openings 830 is aligned directly above and forms a channel that extends through to a corresponding portholes 820. When the vial 20 is secured to the unitary lid 810, medication 15 can be removed from the vial 20 through the porthole 820 and opening 830. An access door 835 is provided to seal each opening 830. The door 835 has a hinge 836 that is secured to top surface 814 of the housing 811, and a latch 837. The door 835 pivots between open and closed positions 838 and 839. Medication 15 is sealed in the container when the vial 20 is secured to the lid 810 and the access door 835 is in its closed position 838. The latch 837 locks the door into its closed position 838. Medication 15 is removed from one of the vials 20 by releasing the appropriate latch 837, moving the corresponding door 835 to its open position 838, inverting the container 800 and pouring the medication out of the associated opening 830.

Figure 28:
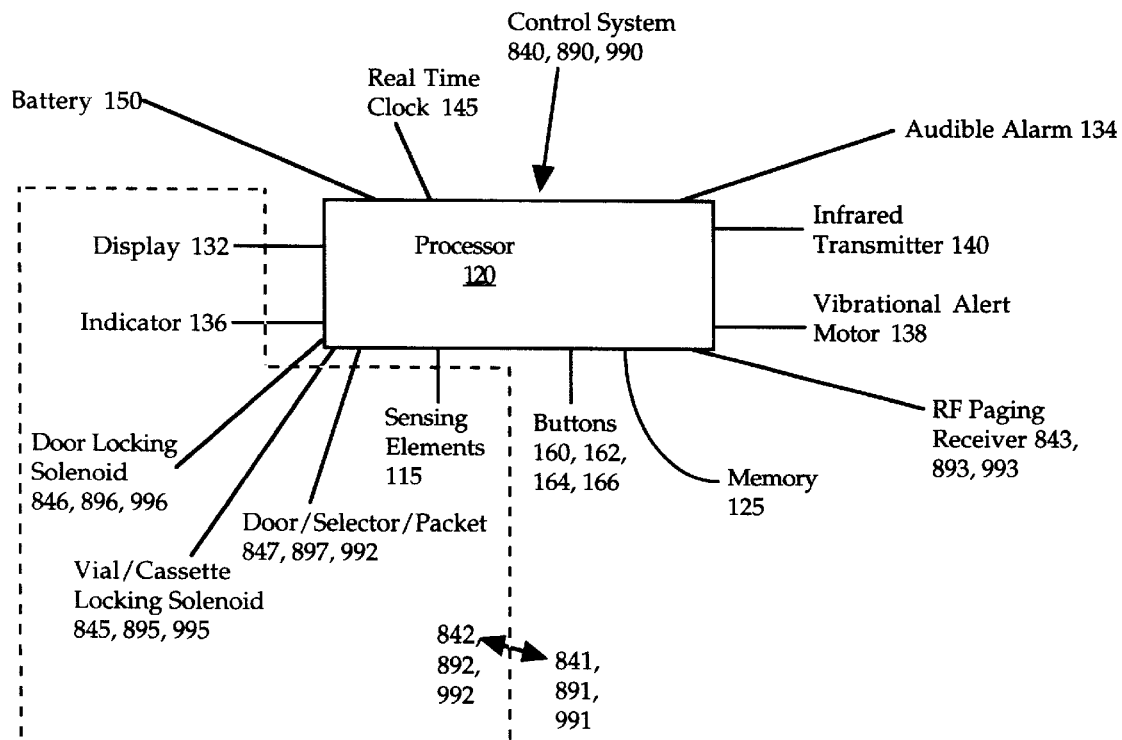
FIG. 28 is a schematic drawing of a circuitry for the multi-vial or multi-blister pack medication container, with the multi-set components grouped at the lower left of the schematic.

As shown in FIG. 28, the unitary lid 810 includes a control system 840 that is similar to the control system 114 of containers 10, 300 and 400 shown in FIG. 9. The control system 840 is broken into two subsets of components 841 and 842. The components forming these two subsets 841 and 842 are the same types of components as in control system 114. The first subset 841 has a one-to-one correlation between components in system 114, and includes computer processor 120, memory 125, audible and vibratory alarms 134 and 138, real time clock 145, battery 150, and buttons 160, 162, 164 and 166. Subset 841 also includes a radio frequency (RF) receiver 843 for receiving information regarding necessary changes in the prescribed dosing regimen 82. Receiver 843 can be a transceiver for transmitting information, such as consumption information 84, back to the pharmacy or prescribing physician. The second subset 842 is broken up into multiple sets of components 844. Each set of components 844 is associated with one particular porthole. Each set of components 844 includes the sensors 115, LCD display 132 and indicator light 136 associated with that particular porthole 820. Each set 844 also includes first and second access control devices 845 and 846, and a sensor 847 for the access door 835 associated with the particular porthole 820 as discussed below. The display 132 and indicator 134 of a particular set 844 are located directly in front of the access door 835 corresponding to the particular porthole 820 and vial 20 for that set. The circuit board 130 is somewhat larger than the board in cap 100 due to the increase in number of components and the spacing apart of the various sets 844 of components along the length of the lid 810.

FIG. 27 shows the vial 20 equipped with machine readable and writable memory strip 60 and contacts 62. The sensors 115 are located on the inside surface of each sensing tab 825. When the vial 20 is secured to its particular porthole 820, the contacts 62 are in electrical communication with the sensors 115 for that porthole. As stated above, the memory strip 60 can be replaced by a memory device that is only machine readable. For example, the vial can be equipped with conductive/non-conductive or reflective/non-reflective surfaces 352-358 as in FIG. 16. Sensing tab 825 and sensors 115 are similar in construction to the sensing tab 372 and sensors 374 of container 300. When the vial 20 is equipped with the conventional bar code in lieu of memory strip 60, the sensors 115 are optical sensors that read the bar coded information when the vial 20 is slid into one of the portholes 820 or rotated into a secure position in that porthole.

As shown in FIG. 28, the control system 840 is equipped with two access control devices 845 and 846. These devices 845 and 846 are similar in design to solenoid locking assembly 180. The first access control device or vial locking solenoid assembly 845 serves the same purpose as assembly 180. Both assemblies 180 and 845 lock the vial 20 to the cap 100 of unitary lid 810 until a predetermined time, such as when the vial is empty. The second access control device or door locking solenoid assembly 846 locks the access door 835 in its closed position 839 to prevent the removal of medication 15 until the prescribed time to take the particular medication contained in the corresponding vial 20. This second access control device 846 includes a solenoid and plunger assembly similar to assembly 180. The plunger engages the latch 837 of the access door 835 to lock the door in its closed position 839. It should be understood that the medication 15 could also be accessed by removing the desired particular vial 20 from the unitary lid 810.

When one particular vials 20 is secured to its associated porthole 820, the information 80 contained in the information strip 60 of that particular vial is received by the sensors 115 associated with that porthole and communicated to the computer processor 120 in the unitary lid 810. This communication of information 80 occurs each time one of the vials 20 is secured to one of the portholes 820 of the unitary lid 810. The processor 120 notes which medication information 80 came from which sensor 115 and corresponding porthole 820 or set 844. The processor 120 uses the its clock 145 and the prescribed dosing regimen information 82 obtained from one sensor 115 and corresponding porthole 820 to compute an appropriate time or times to take the particular medication 15 held by the vial 20 secured to that porthole. The processor 120 then determines the appropriate time or times to take the particular type of medication 15 contained in each of the vials 20 held by its associated porthole 820.

When the processor 120 determines that the time to take one doses of prescribed medication in one particular vial is approaching or has arrived, the processor sends a signal to the display 132 and indicator light 136 for the set 844 associated with the porthole 820 holding that particular type of medication 15. The processor 120 also sends an electric current to the door lock solenoid 846 for that set 844 to release the plunger from engagement with the latch 837 so that the access door 835 is movable to its open position 838. When the door 835 is moved toward its open position 838, the door sensor 847 sends a signal to the processor 120. The processor 120 uses this signal to indicate that the prescribed dose of medication 15 was taken from the corresponding vial 20 at the time the door 835 was opened. This consumption information is stored in the memory 125 of the unitary lid 810. The processor 120 could also send electric current to the vial lock 845 to allow access to the medication 15, and use this occurrence as the signal that medication 15 was consumed. When the memory device 60 on the vial 20 is machine readable and writable, the processor 120 alters the memory device to include this consumption information.

Sixth Embodiment

Figure 29:
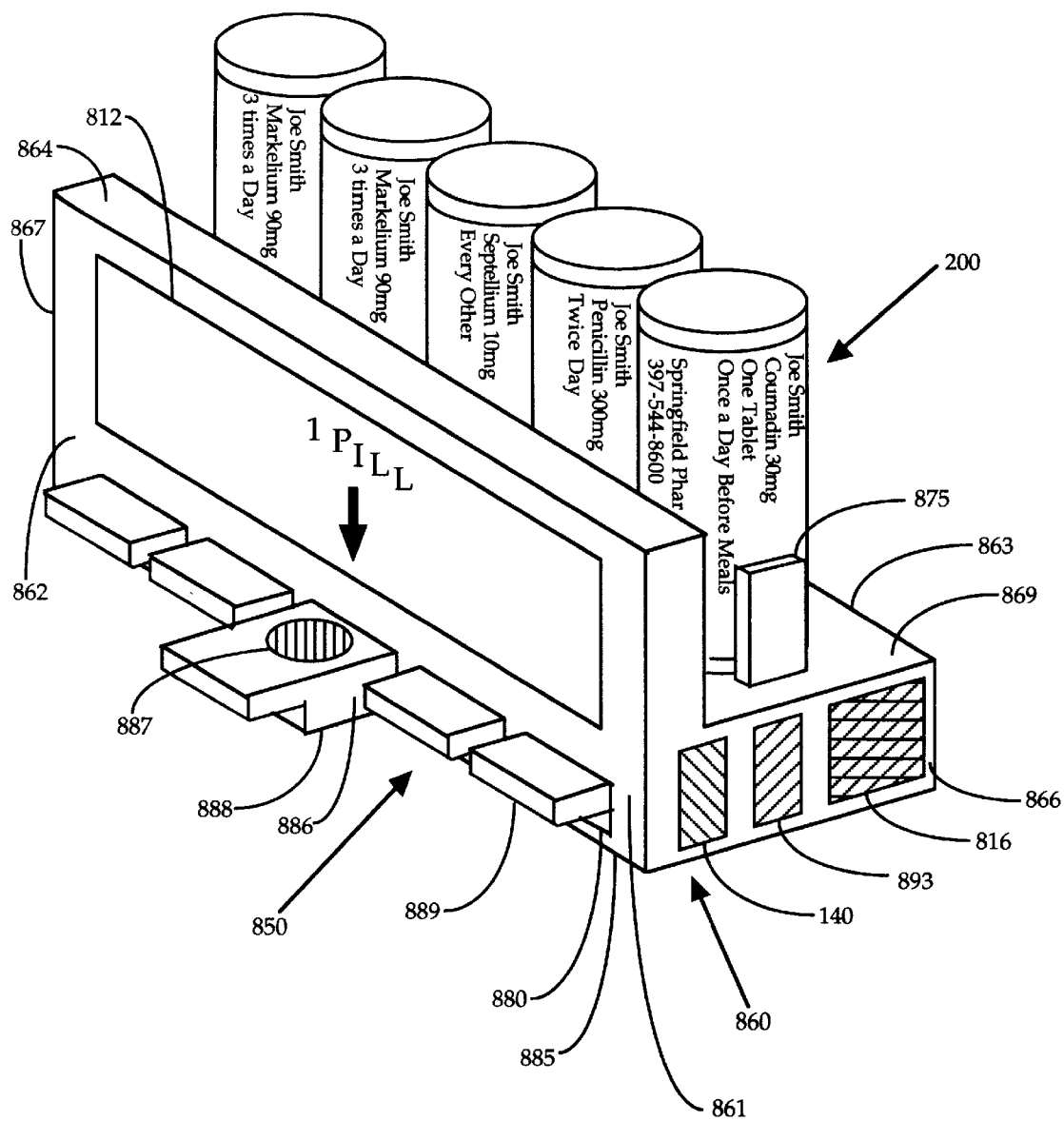
FIG. 29 is a perspective view of a multi-vial medication container with the vials secured to portholes located along a top platform of an L-shaped unitary lid, and the lid containing a single display and several selectors for removing medication from the vials.

FIG. 29 shows a sixth embodiment of the medication container 850 for holding and organizing several different types of medication. This container 850 is similar to the container 800. Each particular vial 20 is physically separable from the other vials, but is removably secured to a unitary lid 860 as discussed below. Each particular vial 20 is equipped with its own corresponding interactive label 50 and machine readable and writable memory strip 60. As in the fifth embodiment, it should be understood that the label 50 of container 850 need not be interactive. The machine readable and writable memory strip 60 can be replaced by a memory device that is only machine readable. For example, memory strip 60 and its contacts 62 and wires 64 can be replaced by the several conductive/non-conductive or reflective/non-reflective surfaces and ground surface 352–358 as in container 300, or by a conventional bar code (not shown) applied to the surface of the label 50.

Figure 30:
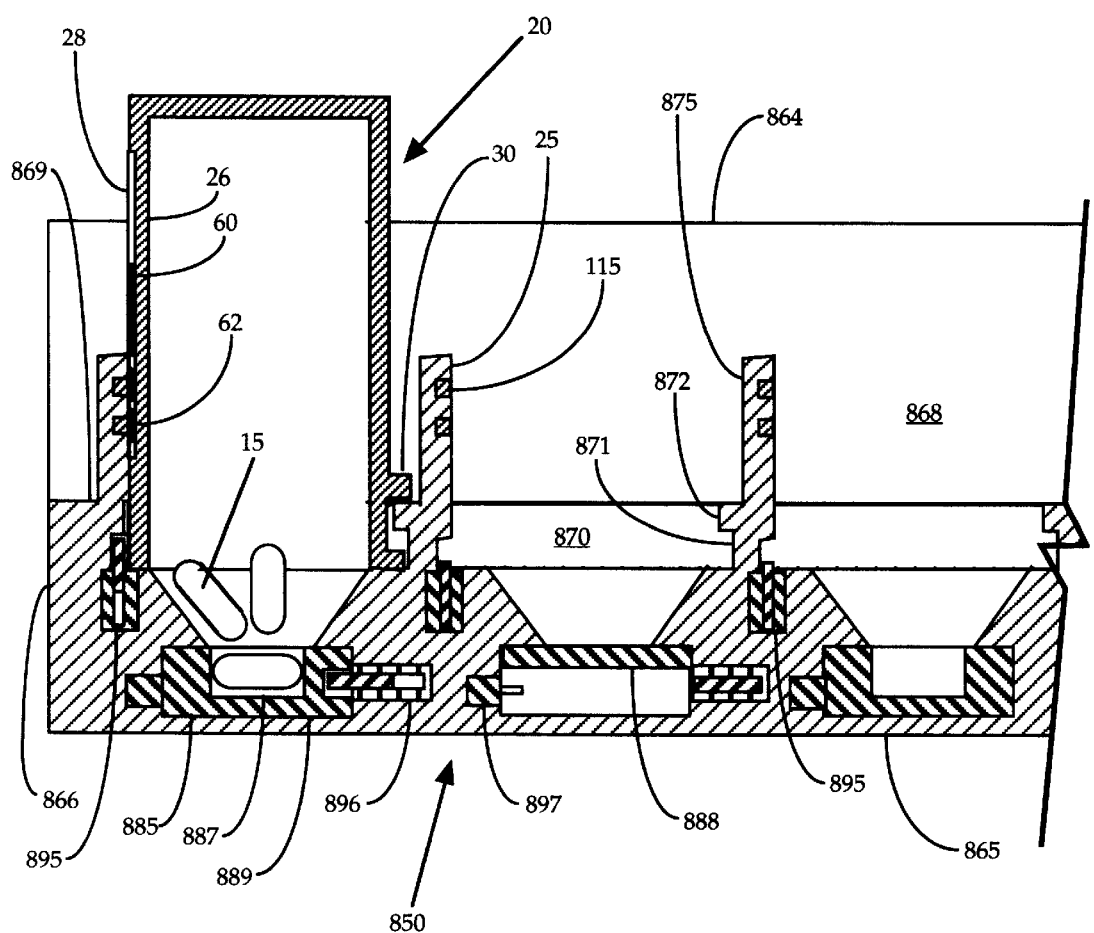
FIG. 30 is a partial, rear cross-sectional view of the multi-vial medication container of FIG. 29 showing one inverted vial secured in an associated porthole with its selector in its closed position, and an adjacent selector in its open position.

The unitary lid 860 includes an L-shaped housing 861 with a front 862, rear 863, top 864, bottom 865, and end surfaces 866 and 867. As best shown in FIG. 30, the housing 861 has an intermediate wall 868 that extends from the top 864 of the housing down to a platform 969 for holding the vials 20. The portholes 870 are similar in construction to the portholes 820 of container 800, and are spaced equidistantly apart from one end 862 of the housing to the other end 863. Each porthole 870 has an inside surface 871 shaped and sized to snugly receive the top end 25 and ratchets 40 of one vial 20. Similar to container 800, the inside surface of each porthole 870 includes several hold down lugs 872 or threads for removably securing the vial 20 to the unitary lid 860. Each particular porthole 870 has a corresponding sensing tab 875 with sensors 15 like those of cap 100. The sensing tabs 875 project upwardly from the top surface 814 of the lid 860, and have an inside surface that is substantially flush with the inside surface 871 of the porthole 870.

Each vial 20 has a guide ring (not shown) similar to guide ring 30 that receives the sensing tab 875. The label 50 is affixed in the recess 28 of the vial 20. The recess 28, guide ring 30 and sensing tab 875 combine to align the textual portion 52 facing toward the front 862 of the unitary lid 860 when the vial 20 is secured. This ensures that each textual portion 52 is visible when several vials 20 are secured to the unitary lid 860. The guide rings 30 also ensure that sensors 876 align with contacts 62 in control system 890 (FIG. 28), or that contacts 192 align with contacts 194 in control system 190 (FIG. 25).

The housing 861 has a number of openings 880 along the length of its front surface 812. Each opening 880 is aligned directly in front of and forms a corresponding channel that extends through to a corresponding porthole 870. When the vial 20 is secured to one of the portholes 870, medication 15 is removed via a medication selector 885. The selector 885 has a shaft 886 that is sized to fit snugly in the opening 880 and its corresponding channel. The shaft 886 has a medication singulating compartment 887 sized to hold a standard dose of medication 15. The selector 885 slides in the channel of the opening 880 to and from open and closed positions 888 and 889. In the closed position 889, the singulating compartment 887 is located inside its corresponding porthole 870 so that one of the doses of medication 15 falls into the compartment. The selector 885 is then pulled partially out of the opening 880 so that the compartment 887 extends beyond the front 862 of the lid so that the medication 15 in the compartment can be removed. Medication 15 is sealed in the container 850 when the vials 20 are secured to the unitary lid 860 and the selector 885 is in its closed position 889.

The unitary lid 810 includes a control system 890 that is similar to control system 840 shown in FIG. 28. The components making up the control systems 840 and 890 are similar. System 890 is broken into two subsets of components 891 and 892. The first subset 891 includes one computer processor 120, memory 125, display 132, audible and vibratory alarms 134 and 138, real time clock 145, battery 150, and buttons 160, 162, 164 and 166. The subset 891 also includes a RF receiver 893 for receiving information regarding necessary changes in the prescribed dosing regimen 82. Receiver 893 can be a transceiver for transmitting information, such as consumption information 84, back to the pharmacy or prescribing physician. The second subset 892 includes multiple sets of components 894. Each set of components 894 is associated with one particular porthole. Each set 894 includes the sensors 115 associated with that particular porthole 870. Each set 894 also includes first and second access control devices 895 and 896, and a sensor 897 for the access door 885 associated with the particular porthole 870 as discussed below. The single LCD display 132 spans the length of the front 862 of the unitary lid 860. The display visually identifies the appropriate selector 885 to pull to obtain the appropriate, prescribed medication 15. The computer processor 120 instructs the display 132 to show an arrow pointing at the appropriate selector 885. Again, the circuit board (not shown) is somewhat larger than circuit board 130 due to the increase in number of components and the spacing apart of the various sets 892 of components along the length of the lid 860.

FIG. 29 shows the vial 20 equipped with machine readable and writable memory strip 60 and contacts 62. The sensors 115 are located on the inside surface of each sensing tab 875. When one of the vials 20 is secured to a particular porthole 870, the contacts 62 of the memory strip 60 are in electrical communication with the sensors 115 for that porthole. As stated above, the memory strip 60 can be replaced by a memory device that is only machine readable. For example, the vial 20 is equipped with conductive/non-conductive or reflective/non-reflective surfaces 352–358 as in FIG. 16. Sensing tab 875 and sensors 115 are similar in construction to the sensing tab 372 and sensors 374 of container 300. When the vial 20 is equipped with the conventional bar code in lieu of memory strip 60, the sensors 115 are optical sensors that read the bar coded information when the vial 20 is slid into one of the portholes 870 or rotated into a secure position in that porthole.

As shown in FIG. 28, the unitary lid 860 is equipped with two access control devices that are similar in design to solenoid locking assembly 180. The first access control device or vial locking solenoid assembly 895 serves the same purpose as assembly 180. Both assemblies 180 and 895 lock the vial 20 to the unitary lid 810 until a predetermined time, such as when the vial is empty. The second access control device or selector locking solenoid assembly 896 locks the selector 881 in its closed position 889 until the prescribed time to take the particular medication in the corresponding vial 20. This second access control device 896 includes a solenoid and plunger assembly similar to assembly 180. The plunger engages the shaft 882 of the selector 881 and locks it in its closed position 889. It should be understood that the medication 15 could also be accessed by removing the desired particular vial 20 from the unitary lid 860.

When one particular vials 20 is secured to its associated porthole 870, the information 80 contained in the information strip 60 of that particular vial is received by the sensors 115 associated with that porthole and communicated to the computer processor 120 in the unitary lid 860. This communication of information 80 occurs each time one of the vials 20 is secured to one of the portholes 870 of the unitary lid 860. The processor 120 notes which medication information 80 came from which sensor 115 and corresponding porthole 870. The processor 120 uses the its clock 145 and the prescribed dosing regimen information 82 obtained from the vial 20 in one particular porthole 870 to compute an appropriate time or times to take the particular medication 15 held by the vial 20 secured to that porthole. The processor 120 then determines the appropriate time or times to take the particular type of medication 15 contained in each of the vials 20 held by their associated portholes 970.

When the processor 120 determines that the time to take one doses of prescribed medication in one particular vial is approaching or has arrived, the processor sends a signal to the display 132 to show an arrow pointing to the associate porthole 870 holding that particular type of medication 15. The processor also sends an electric current to the selector lock solenoid 896 of the appropriate set 894 to release the plunger from engagement with the selector shaft 886 so that the selector 885 for that particular vial 20 is movable to its open position 888. When the selector 885 is moved toward its open position 888, the selector sensor 897 sends a signal to the processor 120. The processor 120 uses this signal to indicate that the prescribed dose of medication 15 was taken from the corresponding vial 20 at the time the selector 885 was moved to its open position 888. This consumption information is stored in the memory 125 of the unitary lid 810. The processor 120 could also send electric current to the vial lock 895 to allow access to the medication 15, and use this occurrence as the signal that medication 15 was consumed. When the memory device 60 on the vial 20 is machine readable and writable, the processor 120 can alter the memory device to include this consumption information.

Seventh Embodiment

Figure 31:
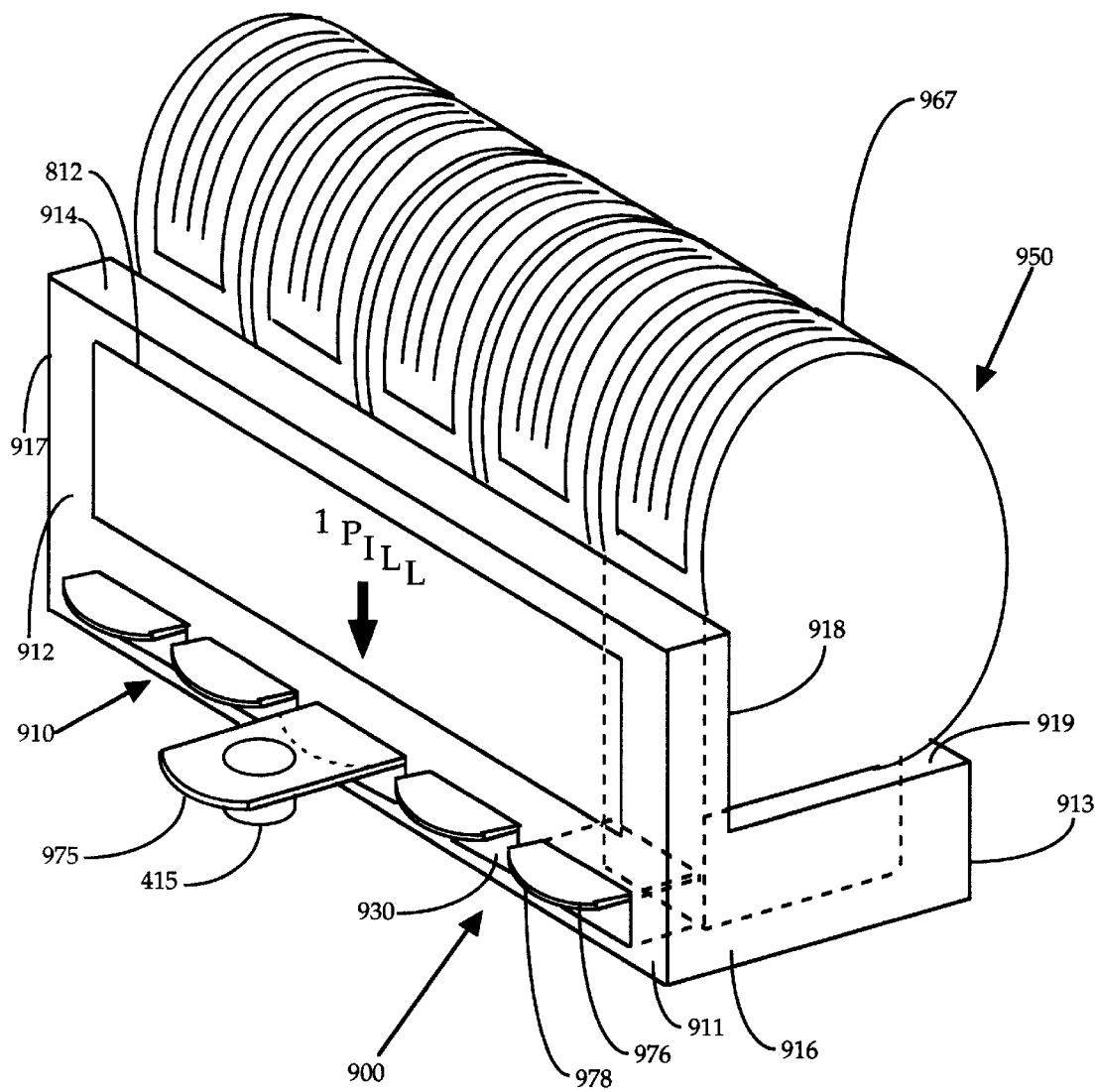
FIG. 31 is a perspective view of a multi-blister cassette medication container, where each cassette is secured to a slot in the top of the platform of the L-shaped unitary lid, and each cassette holds a free end of the blister strip extending through an associated opening in the lid.

FIG. 31 shows a seventh embodiment of the medication container 900 for holding and organizing several different types of medication. This container 900 has an automated, unitary lid 910 that is similar to the unitary lid 860 of container 850. The vials 20 are replaced by blister cassettes 950. Each particular cassette 950 is physically separable from the other cassettes, but is removably secured to a unitary lid 910 as discussed below. Each particular cassette 950 is equipped with its own corresponding machine readable memory device or bar code 960. However, it should be understood that the cassette 950 could contain an interactive label 50. A machine readable and writable memory strip 60 can be substituted for the memory device 960. In addition, several conductive/non-conductive or reflective/non-reflective surfaces and ground surface 352–358 may be substituted as in container 300.

Figure 32:
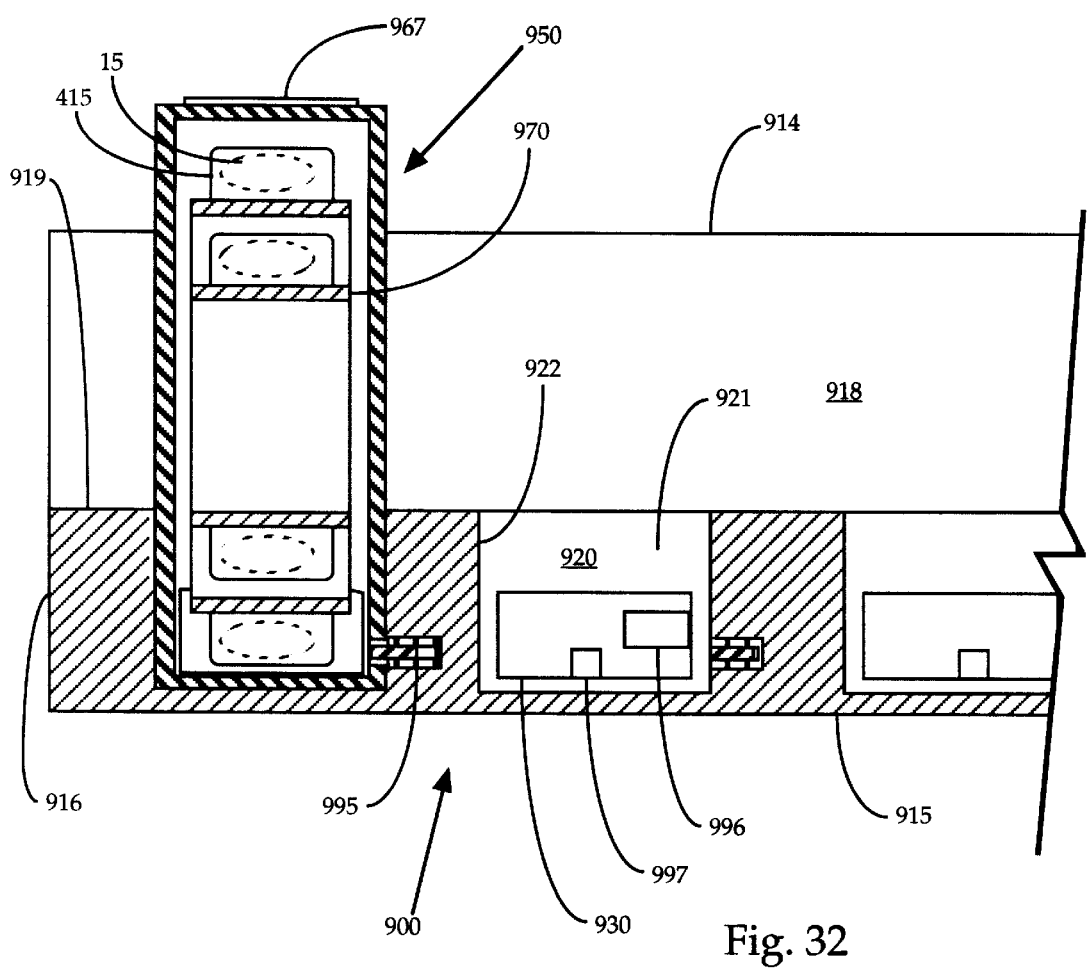
FIG. 32 is a partial, rear sectional view of the container of FIG. 31 showing one blister cassettes secured in its associated slot.

The unitary lid 910 includes an L-shaped housing 911 with a front 912, rear 913, top 914, bottom 915, and end surfaces 916 and 917. As best shown in FIG. 32, the housing 911 has an intermediate wall 918 that extends from the top 914 of the housing down to a platform 919 for holding the blister cassettes 950. The platform 919 has a number of ports or slots 920 formed along the length of its surface. The slots 920 are spaced equidistantly apart from one end 912 of the housing to the other 913. Each slot 920 is formed by a forward wall 921, two lateral walls 922 and a rear wall 923 that are shaped and sized to snugly receive the sides of the cassette 950. The forward wall 921 is flush with the surface of the intermediate wall 918. The housing 911 also has a number of openings 930 formed along the length of its front surface 912. Each opening 930 is aligned directly in front of one of the slots 920. The opening 930 forms a channel extending from the front surface 912, through the lid 910 to the surface of the intermediate wall 918, and into a corresponding slot 920. An optical sensor 940 is secured in the intermediate wall 918 above the opening 930.

Figure 33:
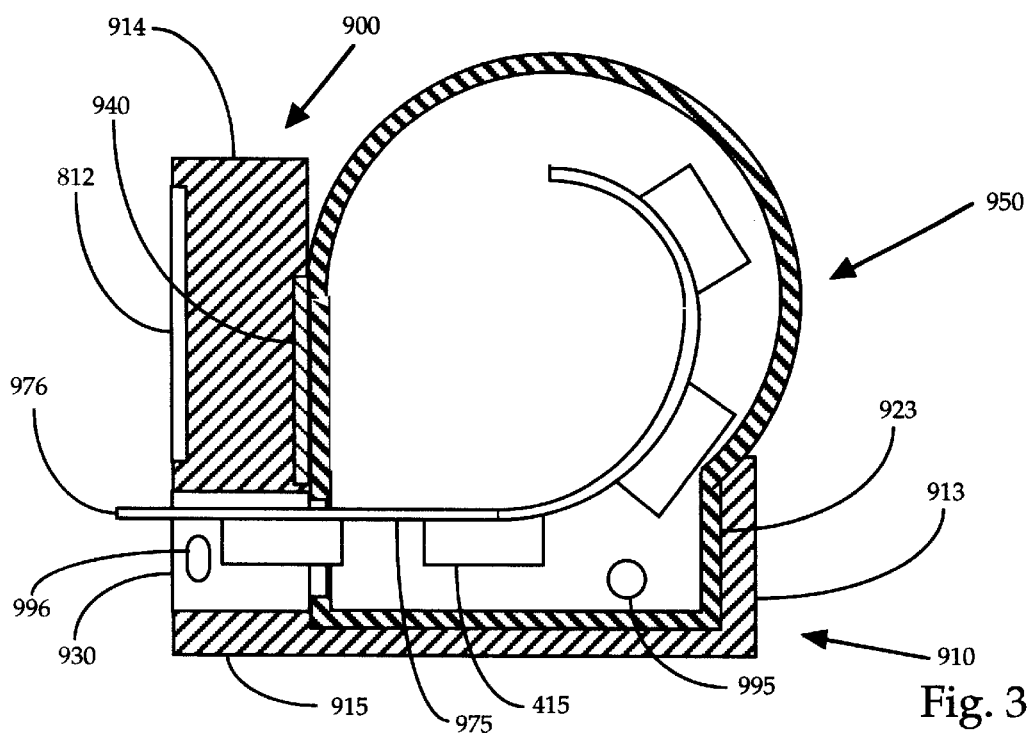
FIG. 33 is a side sectional view of the container of FIG. 31 showing its blister strip coiled inside the cassette with the blister pack at the free end in a reserve position.
Figure 34:
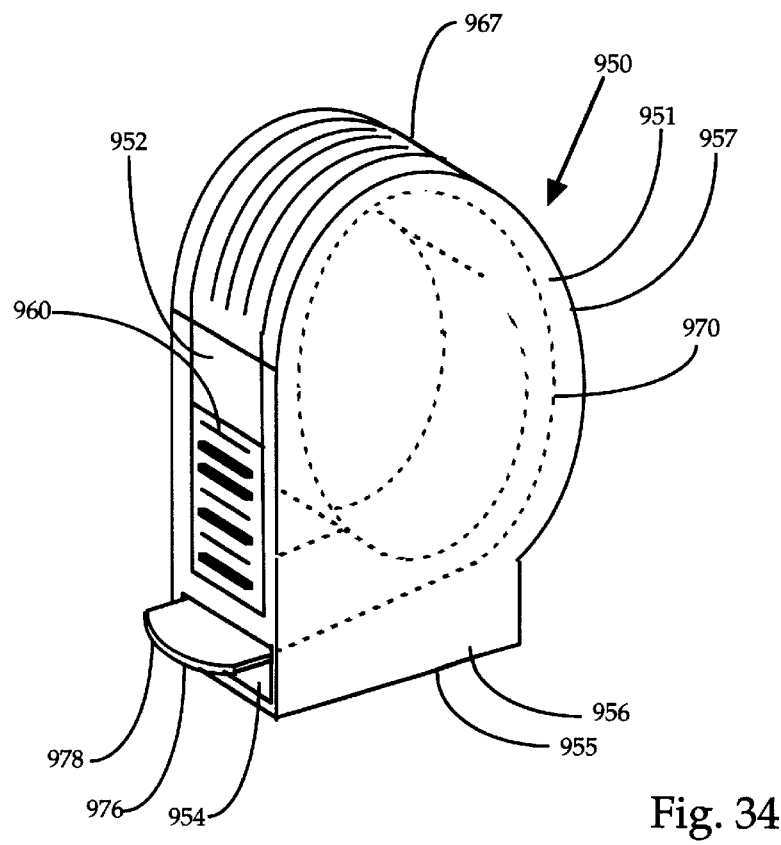
FIG. 34 is a perspective view of the blister cassette used with the medication container of FIG. 31, the cassette being equipped with a bar code memory device.

As best shown in FIG. 33, the blister cassette 950 is formed by a rigid housing 951. The front of the housing 951 is formed by a flat wall 952 with an opening 954 towards its bottom edge. The bottom is formed by a U-shaped channel 955 with lateral rims 956. The top and rear portions of the housing 951 are formed by a circular loop 957. The housing is completed by a pair of flat side walls 958. A machine readable memory device such as bar code 960 is affixed to the front wall 952 above opening 954. The bar code 960 contains a variety of information 80 about the medication 15 in the blister cassette 950. A textual label 967 is affixed to the top or loop portion 957 of the housing 951 so that each label is visible when several cassettes 950 are secured to the unitary lid 910.

The housing 951 holds a conventional blister strip 970 formed by a series of connected blister packets 975 that are separable along a perforation or score line between each adjacent packet. Each blister packet 975 holds a dose of medication 15. The strip 970 is coiled up inside the housing 951 with the outer coil laying against the U-shaped channel 955 between rims 956. A free end 976 of the outer coil passes through the opening 954 in the front wall 952 of the cassette 950.

As shown in FIG. 31, when the blister cassette 950 is secured to the unitary lid 910, the free end 976 of the blister strip 970 extends through opening 930. This places the end packet 975 in a reserve position 978. Medication 15 is obtained by pulling the end packet 975 completely through the opening 930, and tearing off the end packet 975 along the perforated line connecting it to its adjacent packet. The adjacent packet is now in the reserve position 978 with its free end 976 partially extending through opening 930, and is accessible when the next dose of medication is due to be taken.

The unitary lid 910 includes a control system 990 that is similar to control system 890 shown in FIG. 28. The components making up control systems 890 and 990 are similar. System 990 are broken into two subsets of components 991 and 992. The first subset 991 includes one computer processor 120, memory 125, display 132, audible and vibratory alarms 134 and 138, real time clock 145, battery 150, and buttons 160, 162, 164 and 166. The first subset 991 also includes a RF receiver 993 for receiving information regarding necessary changes in the prescribed dosing regimen 82. Receiver 993 can be a transceiver for transmitting information, such as consumption information 84, back to the pharmacy or prescribing physician. The second subset 992 includes multiple sets 994. Each set of components 994 is associated with one particular slot 920. Each set of components 994 includes the sensors 1 15 associated with that particular slot 920. Each set 994 also includes first and second access control devices 995 and 996, and a sensor 997 for the opening 930 associated with the particular slot 920 as discussed below. The single LCD display 132 spans the length of the front 912 of the unitary lid 910. The display visually identifies the appropriate blister packet 975 to pull to obtain the appropriate, prescribed medication 15. The computer processor 120 instructs the display to point an arrow at the appropriate packet 975. Again, the circuit board (not shown) is somewhat larger than circuit board 130 due to the increase in number of components and the spacing apart of the various sets 992 of components along the length of the lid 910.

Optical sensors 940 are located on the surface of the intermediate wall 918. When one of the blister cassettes 950 is slid into place in a particular slot 920, the optical sensor 940 corresponding to that slot reads the information 80 contained in the memory device or bar code 960. When the cassette 950 is equipped with machine readable and writable memory strip 60 in lieu of bar code 960, the optical sensors 940 are replaced with sensors 115. When the cassette 950 is equipped with conductive/non-conductive or reflective/non-reflective surfaces 352-358, the sensors 115 are similar in construction to sensors 374 of container 300.

As shown in FIG. 28, the control system 990 is equipped with two access control devices that are similar in design to solenoid locking assembly 180. The first access control device or cassette locking assembly 995 prevents the removal of the cassette 950 from the unitary lid 910 until a predetermined time, such as when the cassette is empty. The second access control device or solenoid locking assembly 996 prevents the extension of free end 976 of the blister strip 975 through opening 930 until the prescribed time to take the particular medication in the corresponding cassette 950. This second access control device 996 includes a solenoid and plunger assembly. The plunger engages the blister strip 975 and locks it in place so that it cannot be pulled out of the opening 930. It should be understood that the medication 15 could also be accessed by removing the desired particular vial 20 from the unitary lid 910.

When one particular cassette 950 is secured to its associated slot 920, the information 80 contained in the information strip 60 of that particular cassette is received by the sensors 115 associated with that slot and communicated to the computer processor 120 in the unitary lid 910. This communication of information 80 occurs each time one of the cassettes 950 is secured to one of the slots 920 of the unitary lid 910. The processor 120 notes which medication information 80 came from which associated sensor 115 for the particular slot 920. The processor 120 uses the its clock 145 and the prescribed dosing regimen information 82 obtained from the particular cassette 950 secured to its associate slot 920 to compute an appropriate time or times to take the particular medication 15 held by that cassette. The processor 120 then determines the appropriate time or times to take the particular type of medication 15 contained in each of the cassette 950 held by the slots 920.

When the processor 120 determines that it is time to take one doses of prescribed medication in one particular cassette 950, the processor sends a signal to the display 132 to show an arrow pointing to the associate slot 920 and cassette 950 holding that particular type of medication 15. The processor also sends an electric current to the blister strip locking solenoid 996 of the appropriate set 994 associated with slot 920 to withdraw the plunger from in front of the leading blister packet 975 so that this packet can be removed from its associated opening 930. When the blister packet 975 is removed and an other blister packet is advanced to the reserve position 978, the selector sensor 997 sends a signal to the processor 120. The processor 120 uses this signal to indicate that the prescribed dose of medication 15 was taken from the corresponding cassette 950 at the time the blister packet 975 was removed. This consumption information is stored in the memory 125 of the unitary lid 910. The processor 120 could also send electric current to the vial lock 995 to allow access to the medication 15, and use this occurrence as the signal that medication 15 was consumed. When the memory device 60 on the cassette 950 is machine readable and writable, the processor 120 can alter the memory device to include this consumption information.

Operation of Fifth, Sixth and Seventh Embodiments

The following is provided to assist the reader in understanding the operation of the preceding embodiments of the invention. When a physician prescribes one or more medications to a particular patient, the prescription is forwarded to a pharmacy. The pharmacist or his or her staff uses the prescription to fill one or more vials 20 or cassettes 950 with the prescribed medications 15. For each vial 20 or cassette 950, the pharmacy creates prescription information 80 corresponding to the type of medication 15 placed in that vial or cassette. This information 80 is written or otherwise applied to the memory device 60, 352–358 or 960 that is secured or otherwise applied to the appropriate vial 20 or cassette 950. This information 80 includes dosage and time frequency information for the particular medication 15 in that vial 20 or cassette 950. The pharmacy staff, a healthcare worker or patient then secures the separate vials 20 or cassettes 950 to the unitary lid 810, 860 or 910 assigned to or owned by that particular patient.

The medication containers 800, 850 and 900 hold and organize several vials 20 or cassettes 950. Each unitary lid 810, 860 or 920 has several ports 820, 870 or 920 for receiving the vials 20 or cassettes 950. Each port 820, 870 or 920 has one corresponding pair of sensors 115 or 374 for reading the information 80 contained in the memory device 60, 352-358 or 960 of the vial 20 or cassette 950. Each port 820, 870 or 920 also has one corresponding opening 830, 880 or 930 through which the medication 15 in corresponding vial 20 or cassette 950 is dispensed. Each container 800, 850 or 900 includes a control system 840, 890 or 990, respectively, that includes a processor 120 for controlling the operations of the container.

The processor 120 organizes the activation of the display(s) 132 and alarm(s) 134, 136 and 138 for instructing and alerting the patient when it is time to consume one of the prescribed medications 15 held by the container. When the vials 20 or cassettes 950 are secured to the unitary lid 810, 860 or 960, the processor 120 reads the prescription information 80 from the memory device 60, 352–358 or 960, and calculates the appropriate time to take each of the medications 15 contained in the several vials 20 or cassettes 950.

The computer processor 120 uses the prescribed dosing regimen information 82 and the timing device 145 to calculate or otherwise develop the prescribed times for taking each of the different medications 15 held in the container 800, 850 or 900. The processor 120 uses its timing device 145 to determine when the predetermined time or times to take one of the particular types of medication occur. The computer processor then informs the patient that it is time to take a dose of medication 15 via the display 132, indicator 136, or other various alarms 134 and 138. Information 80 is also communicated to the processor 120 and memory 60, 125 via electrical contacts or via an RF or magnetically coupled link.

When the processor 120 determines that at least one medication 15 is due, the processor issues an audible alert using speaker 134. This alert can be in the form of a voice synthesized message that indicates the correct vial 20 or cassette 950 to access and amount of medication to consume. The processor 120 also instructs the LCD display 132 to show a message or the indicator light 136 to flash directly in front of the appropriate vial 20 or cassette 950 containing the prescribed medication 15 to be taken at this time, and the amount of that medication to take.

The control systems 840, 890 or 990 operate in much the same way as control system 114 to obtain consumption information. The vials 20 and cassettes 950 are secured and locked to the ports 820, 870 or 920 of the container 800, 850 or 900 by first access control mechanism 845, 895 or 995.

Each vial 20 or cassette 950 has an opening 830, 880 or 930 for removing medication 15. The vial openings 830 or 880 are closed by door 835 or selector shaft 885. The door 835 or shaft 885 is locked closed 839 or 889 by a second access control mechanism 846 or 896. The blister cassette 900 prevents individual blister packs 975 from being pulled from opening 930 by second access control mechanism 996. At the appropriate prescribed time, the processor 120 sends electrical current to the second access control mechanism 846, 896 or 996 to unlock the door 835, selector 885 or blister packet 975.

Container 800 requires the appropriate access door 835 corresponding to the particular vial 20 containing the prescribed medication 15 to be moved to its open position 838 from its corresponding porthole 820 to remove medication. When the door 835 or selector shaft 885 is moved to its open position 838 or 888, the sensor 847 or 897 sends a signal to processor 120 indicating that the appropriate dose or doses of medication 15 has been removed and consumed. When the machine readable and writable memory device 60 is used, the processor 120 writes to or otherwise alters the memory strip 60 to note this consumption information 80.

The medication containers 800, 850 and 900 compare the several medications 15 contained in their vials 20 or cassettes 950 by comparing the information 80 in each of their corresponding memory strips 60. For example, the processor 120 references and compares the lists of contraindicated medications that are part of the medication information 84. Should the processor 120 determine that two or more types of medications 15 secured to the unitary lid 810, 860 or 960 are contraindicated, the processor will display an appropriate message on the display 132 or activate one of the alarms 134, 136 or 138 to communicate this to the patient. Every time a medication 15 is issued to a patient, the most recent list of contraindications is included in the memory strip 60 or 960 of the vials 20 or cassettes 950. A list of contraindicated medications can also be maintained in the memory 125 of the lid 810, 860 or 910.

The memory 125 of each organizer 800, 850 or 900 is loaded with information containing a list of medications for whom the particular patient is known to be allergic. The organizer 800, 850 or 900 will alert the patient or care giver if one of the vials 20 or cassettes 950 secured to the unitary lid 810, 860 or 910 contains medication identified as being one of the medications in the list of allergic medications. The list of allergic medications can be downloaded from a pharmacy workstation to the memory 125 prior to giving the unitary lid to the particular patient or their care giver. The list of allergic medications can also be downloaded from the memory device 60 or 960 of one of the vials 20 or cassettes 950 secured to the unitary lid 810, 860 or 960. The processor 120 then compares each type of medication contained by the vials 20 or cassettes 950 secured to the unitary lid to the list of allergic medications to determine if one of the vials or cassettes contains an allergic medication. If an allergic medication is identified, the processor 120 indicates an appropriate message on the display 132 or activate one of the alarms 134, 136 or 138 to warn the patient or care giver that the particular patient is allergic to one of the types of medications contained in one of the vials 20 or cassettes 950.

When medications are prescribed for consumption in paired dosing regimens, this information is noted by the pharmacy on the memory strip 60 or 960, and communicated to the processor 120 when the vial 20 or cassette 950 is secured to the unitary lid 810, 860 or 960. The memory strip 60 or 960 contains information identifying that this type of medication 15 is prescribed for use with an other type of medication. The memory strip 60 or 960 also contains information identifying this other type of medication. The processor 120 uses the prescription information 80 of both memory strips 60 or 960 to determine an appropriate medication schedule such as drug A on Monday, drug B on Tuesday, drug A on Wednesday, etc. The organizer 800, 850 or 900 alerts the patient via the display 132 or audible alarm 134 if one paired medication is attached to the organizer, but the other is not. The processor 120 checks the information received from the various memory devices 60 or 960 of the vials 20 or cassettes 950 secured to the unitary lid 810, 860 or 969 to ensure that vials or cassettes containing both types of paired medications 15. The processor 120 displays an appropriate message on the display 132 or activates an alarm 134, 136 or 138 if information identifying both types of paired medications 15 have not been received.

Each organizer 800, 850 or 900 contains medication prescribed or otherwise intended for a particular individual. The organizer 800, 850 or 900 will alert that individual if one of the vials 20 or cassettes 950 secured to the unitary lid 810, 860 or 910 contains medication intended for an individual other than this particular individual. For example, if one family member inadvertently secures the vial 20 or cassette 950 containing one type or strength of medication prescribed for another family member to their unitary lid 810, 860 or 910, the container 800, 850 or 900 will alert the individual of this fact. The memory device 60 or 960 of each vial 20 or cassette 950 contains information that identifies the particular person for whom the medication is prescribed or prescribed person information. The memory 125 of the unitary lid 810, 860 or 960 is provided with particular patient information that identifies the person that should be using the unitary lid. The particular patient information can be downloaded from a pharmacy workstation to the memory 125 prior to giving the unitary lid to the particular patient or their care giver. The particular patient information can also be downloaded from the memory device 60 or 960 of a first vial 20 or cassette 950 secured to the unitary lid 810, 860 or 960. In this case, the particular patient information is the same as the prescribed information contained in the memory device 60 or 960 of that first vial 20 or cassette 960 secured to the unitary lid 810, 860 or 960. The computer 120 then compares the particular patient information to the prescribed patient information to determine if they identify the same patient. If the two sets of patient information do not identify the same patient, the processor 120 indicates an appropriate message on the display 132 or activate one of the alarms 134, 136 or 138 to warn the patient or care giver that the particular type of medication in the vial 20 or cassette 950 is not intended for this particular patient.

When the processor 120 determines that two different medications 15 are to be taken at the same time, the organizer 800, 850 or 900 signals the indicator 136 to flash or the display 132 to indicate a message instructing the patient to consume the proper amount of each medication. The processor 120 instructs the patient to take one type of medication 15 at a time. The patient is alerted to each appropriate prescribed medication in sequence. This sequencing avoids telling the patient to simultaneously obtain two pills from a first vial 20 or cassette 950 and one pill from a second vial or cassette. Many patients may get confused and dispense them in the opposite quantities. With respect to container 800, since in the patient is removing the medication via the access doors 835, they may accidentally remove too many pills from each door, and return them to the wrong vial 20.

As in container 10, the containers 800, 850 and 900 include buttons 160, 162, 164 and 166 that electromechanically communicate information to the processor 120. By pressing one of the buttons, the patient is able to send an electrical signal to the processor 120 in response to a question shown on the display 132 or to indicate an action to be taken, such as turn off an alert or alarm 134 or 136. Other buttons are located on the bottom surface 815, 875 or 915 of the lid 810, 860 or 910 to enable the patient to set the correct date, hour and minute of the real time clock 145 that is in electrical communication with the processor 120 via the circuit board 130.

It should also be understood that the invention as a whole may be embodied in other specific forms without departing from the spirit or central characteristics thereof. The present examples and embodiments thereof are to be considered in all aspects as illustrative and not restrictive, and the invention is not to be limited to the details given herein. It will be understood by those of skill in the art that various changes may be made and equivalents may be substituted without departing from the broader aspects of the invention. Specifically, while the invention has been shown and described as including a vial, blister pack or cassette container, it should be understood that other forms of containers could be used with equal effectiveness. For example, the container could be a tray or a cassette that does not include a cap, cover or lid. The memory device or memory strip could also communicate with the processor of the container via RF technology. It should therefore be understood that the container can take on a variety of shapes and forms without departing from the broad aspects of the invention.

I claim:

1. A medication container for organizing different types of medication comprising:

a plurality of separate and particular vials, each of said particular vials having an inside surface that defines a compartment, said compartment of each of said particular vials being adapted to hold a particular type of medication;

a plurality of machine readable memory devices, each of said particular vials having a corresponding memory device, each of said corresponding memory devices being adapted to contain prescribed dosing information corresponding to said particular type of medication in said particular vial;

a unitary lid having a plurality of particular ports, each of said particular vials being removably securable to one of said particular ports, said lid further having a plurality of sensors, each particular port having a corresponding sensor, and each corresponding sensor communicating with said corresponding memory device of said particular vial secured to said particular port, said unitary lid having a computer processor in electrical communication with a timing device, a communication device, and said plurality of sensors, said prescribed dosing regimen information contained in each of said memory devices being transmitted to said computer processor when each of said particular vials are secured to their said particular ports, said computer processor using said timing device and said prescribed dosing regimen information from each of said memory devices to develop a predetermined time to take each of said particular types of medication, and said computer processor communicating said predetermined time to said communication device.

2. The medication container of claim 1, and wherein said communication device includes a display that indicates said particular vial from which said particular type of medication is to be taken.

3. The medication container of claim 2, and wherein said unitary lid has a predetermined length and said ports are aligned linearly along said length of said lid, and said display spans said length of said lid and is positioned in front of each port.

4. The medication container of claim 1, and wherein said unitary lid has a predetermined length and said ports are aligned linearly along said length of said lid, and said communication device includes several particular displays, each particular display being positioned in front of one of said particular ports.

5. The medication container of claim 1, and wherein said unitary lid includes a receiver for obtaining updated prescription dosing information.

6. The medication container of claim 1, and wherein each of said plurality of ports has a corresponding opening, and said particular type of medication held in said particular vial secured to its said particular port is removed via said corresponding opening.

7. The medication container of claim 6, and wherein each of said corresponding openings has an access door that is movable from a closed position to an open position to remove said particular type of medication from said particular vial.

8. The medication container of claim 6, and wherein each of said corresponding openings includes a selector that is movable from open and closed positions for obtaining one dose of medication from said compartment of said particular vial secured to said particular port.

9. The medication container of claim 6, and wherein each of said ports includes an access control device, each of said access control devices being adapted to prevent removal of said particular type of medication from said corresponding opening until said predetermined time occurs.

10. The medication container of claim 9, and wherein said access control device is a locking mechanism located in said lid, and said locking mechanism prevents removal of said vial from said lid until said predetermined time occurs.

11. The medication container of claim 1, and wherein each of said particular vials has a guide ring with an opening aligned with said memory strip secured to said particular vial, and said corresponding sensor is located on a corresponding sensing tab, and said guide ring and corresponding sensing tab cooperate to facilitate communicative alignment of said corresponding sensor with said memory strip.

12. The medication container of claim 1, and wherein said memory strip contains contraindication information and said processor sends a signal to the communication device when one particular vial containing one particular type of medication is determined by said processor to be contraindicated with an other particular vial containing an other particular type of medication.

13. The medication container of claim 1, and further comprising a plurality of second sensors, each particular port having a corresponding second sensor, each second sensor determining when medication is removed from said vial particular vial secured to said particular port.

14. The medication container of claim 1, and wherein said memory device is machine readable and writable, and said memory device is alterable to contain one of either actual consumption information and updated prescription information.

15. A medication container for organizing different types of medication comprising:

a plurality of separate and particular cassettes, each of said particular cassettes having an inside surface that defines a compartment, and said compartment of each of said particular cassettes being adapted to hold a particular type of medication;

a plurality of machine readable memory devices, each of said particular cassettes having a corresponding memory device, each of said corresponding memory devices being adapted to contain prescribed dosing information corresponding to said particular type of medication in said particular cassette;

a unitary lid having a plurality of particular ports, each particular cassette being removably securable to one of said particular ports, said lid further having a plurality of sensors, each particular port having a corresponding sensor, and each corresponding sensor communicating with said corresponding memory device of said particular cassette secured to said particular port, said unitary lid having a computer processor in electrical communication with a timing device, a communication device, and said plurality of sensors, said prescribed dosing regimen information contained in each of said memory devices being transmitted to said computer processor when said particular cassettes are secured to their said particular ports, said computer processor using said prescribed dosing regimen information and said timing device to develop a predetermined time to take each particular type of medication, and said computer processor communicating said predetermined time to said communication device.

16. The medication container of claim 15, and wherein each of said plurality of ports has a corresponding opening, and said particular type of medication held in said particular cassette secured to its said particular port is removed via said corresponding opening.

17. The medication container of claim 16, and wherein each of said cassettes is a blister strip cassette holding a blister strip, and a free end of said blister strip projects through said corresponding opening.

18. The medication container of claim 15, and wherein said communication device includes a display and said display indicates the particular cassette from which the particular type of medication is to be taken.

19. The medication container of claim 15, and wherein said unitary lid has a predetermined length and said ports are aligned linearly along said length of said lid, and said display spans said length of said lid so as to be positioned in front of each port.

20. The medication container of claim 15, and wherein said unitary lid includes a receiver for obtaining updated prescription dosing information.

21. The medication container of claim 20, and wherein said memory device is machine readable and writable, and wherein said memory device is altered to contain said updated prescription dosing information.

22. The medication container of claim 17, and wherein each of said ports includes an access control device, each of said access control devices being adapted to prevent removal of said particular type of medication in said blister strip from said corresponding opening until said predetermined time occurs.

23. The medication container of claim 15, and wherein said memory strip contains contraindication information and said processor sends a signal to the communication device when one particular cassette containing one particular type of medication is determined by the processor to be contraindicated with an other particular cassette containing an other particular type of medication.

24. The medication container of claim 15, and farther comprising a plurality of second sensors, each particular port having a corresponding second sensor, each second sensor determining when medication is removed from said cassette particular cassette secured to said particular port.

25. The medication container of claim 15, and wherein said memory device is machine readable and writable, and said memory device is altered to contain actual consumption information.

26. A method of detecting contraindicated medications, the detection method comprising the steps of:

providing a unitary lid and a plurality of containers, said unitary lid having a computer processor, an associated memory and a plurality of ports, each of said containers holding a particular type of medication and having a memory device containing medication type information that identifies the type of medication in said container, one of either of said associated memory and said memory device having a list of contraindicated medications;

joining each of said containers to one of said ports;

communicating said medication type information in said memory device of each of said containers and said list of contraindicated information to said computer processor;

using said processor to compare said medication type information from each of said containers with said list of contraindicated medications, and to determine when said medication type information of two of said containers are contraindicated; and, communicating that said containers contain contraindicated medications.

27. The detection method of claim 26, and wherein said container is one of either a vial or a cassette.

28. A method of detecting medication for whom a particular person is known to be allergic, the detection method comprising the steps of:

providing a lid having a memory containing allergy information that identifies each of the medications for which the particular person is allergic, and further providing a container holding the medication and having a memory device containing medication type information, and either of said lid and said container having a computer processor;

joining said container to said lid;

communicating said allergy information and said medication type information to said computer processor;

using said processor to compare said allergy information with said medication type information, and to determine when said allergy information matches said medication type information; and, communicating that the particular person is allergic to the medication.

29. The detection method of claim 28, and wherein said container is one of either a vial or a cassette.

30. A method of ensuring that a medication is prescribed for a particular person, the ensuring method comprising the steps of:

providing a lid having a memory containing particular person information that identifies the particular person, and firthier providing the particular person with a container holding the medication and having a memory device containing prescribed person information, and either of said lid and said container having a computer processor;

joining said container to said lid;

communicating said particular person information and said prescribed person information to said computer processor;

using said processor to compare said particular person information with said prescribed person information, and to determine when said particular person information differs from said prescribed person information; and, communicating that the medication is not intended for the particular person.

31. The ensuring method of claim 30, and wherein said container is one of either a vial or a cassette.

32. A medication container for containing doses of medication, said medication container comprising:

a first piece having inside and outside surfaces, said inside surface defining a compartment, and said compartment containing the medication;

a machine readable and writable, memory strip containing prescribed dosing regimen information for the medication, said memory strip being secured to said first piece;

a second piece adapted for removable securement to said first piece, said second piece having a sensor positioned to communicate with said memory strip when said second piece is secured to said first piece, said second piece having a timing device and a communication device, said timing device, communication device and sensor being in electrical communication with a computer processor, said prescribed dosing regimen information in said memory strip being transmitted to said computer processor when said first piece is secured to said second piece, said computer processor using said prescribed dosing regimen information and said timing device to develop a predetermined time to take the medication, and said computer processor communicating said predetermined time to said communication device; and, wherein movement of said second piece allowing access to the medication causes said computer processor to obtain consumption time information corresponding to said movement of said second piece, and said consumption time information is recorded in said memory strip.

33. The medication container of claim 32, and wherein said first piece is a cassette holding a blister strip having a plurality of packets, each of said packets holding one of the doses of the medication, and said second piece is a lid that holds said cassette.

34. The medication container of claim 33, and wherein said lid includes an opening through which said blister packs are removed, and said lid includes an access control device adapted to prevent advancement of one of said packets through said opening until said predetermined time occurs.

35. The medication container of claim 33, and wherein said lid includes an access control device that prevents removal of said cassette from said lid.

36. The medication container of claim 33, and wherein said lid includes a second sensor for sensing when one of the doses of the medication is removed from said container.

37. The medication container of claim 33, and wherein said memory strip contains a program for determining said predetermined time information, said program being communicated to the processor when said memory strip is aligned with said sensor, said program enabling said container to allow access to one of the packets at said predetermined time.

38. The medication container of claim 33, and further including a plurality of separate and particular cassettes, each of said cassettes having a corresponding memory device, and wherein said lid has a plurality of ports, each of said ports having a corresponding sensor in communication with said computer processor, each of said particular cassettes being adapted for removable securement to a corresponding port, said corresponding sensor sensing said information of said corresponding memory device of said particular cassette secured to said corresponding port, wherein movement of said lid allowing access to the medication of said particular cassette secured to said corresponding port causes said computer processor to obtain consumption time information corresponding to said movement, and said consumption time information is recorded in said memory strip.

39. A medication container for containing doses of medication, said medication container comprising:
- a first piece having inside and outside surfaces, said inside surface defining a compartment, and said compartment containing the medication;
- a machine readable and writable memory strip containing quantity information regarding the quantity of the doses of medication in said first piece, said memory strip being secured to said first piece; and,
- a second piece adapted for removable securement to said first piece, said second piece having a sensor positioned to communicate with said memory strip when said second piece is secured to said first piece, said sensor being in electrical communication with a computer processor, and said information in said memory strip being transmitted to said computer processor when said first piece is secured to said second piece, and said sensor senses removal information corresponding to a removal of the medication from said first piece, said sensor communicating said removal information to said computer processor, and said computer processor altering said quantity information in said memory strip to indicate that said quantity of medication in said first piece has been reduced.

40. The medication container of claim 39, and wherein said first piece is a cassette holding a blister pack having a plurality of pockets, each pocket containing one of the doses of medication, and said second piece is a lid that holds said cassette.

41. The medication container of claim 40, and wherein said lid includes an opening for allowing access to one of said blister packs.

42. The medication container of claim 41, and wherein said lid includes a separate sensor for sensing said removal information, and said separate sensor senses when the medication passes through an opening in said lid.

43. The medication container of claim 41, and wherein said lid includes an access control device that prevents advancement of said blister pack through said opening in said lid until said predetermined time has occurred.

44. The medication container of claim 40, and wherein said lid includes a timing device and a communication device in electrical communication with said computer processor, and said memory strip includes prescribed dosing regimen information, and said computer processor uses said prescribed dosing regimen information and said timing device to develop a predetermined time to take the medication, and said computer processor communicates said predetermined time to said communication device.

45. The medication container of claim 44, and wherein said computer processor obtains removal time information from said timing device corresponding to said removal information, said computer processor communicating said removal time information to said memory strip.

46. The medication container of claim 43, and wherein said memory strip contains a program for developing said predetermined time, said program being communicated to said computer processor when said memory strip is in communication with said sensor, said program enabling said access control device to dispense the medication at said predetermined time.

47. The medication container of claim 40, and wherein said memory strip contains prescription information, and said lid further includes means for communicating said prescription information to a separate computer.

48. The medication container of claim 42, and further including a plurality of separate and particular cassettes, each of said cassettes having a corresponding memory device, and wherein said lid has a plurality of ports, each of said ports having a corresponding sensor and a corresponding separate sensor in communication with said computer processor, each of said cassettes being adapted for removable securement to a corresponding port of said plurality of ports, said corresponding sensor sensing said information on said corresponding memory device of said particular cassette secured to said corresponding port, each of said separate sensors sensing removal information corresponding to its said corresponding cassette and communicating said removal information to said computer processor, and said computer processor altering said quantity information in said corresponding memory strip to indicate that said quantity of medication in said corresponding cassette has been reduced.

* * * * *